(12) United States Patent
Mohanty

(10) Patent No.: US 11,579,114 B2
(45) Date of Patent: Feb. 14, 2023

(54) FOUR POINT SEMICONDUCTOR NANOWIRE-BASED SENSORS AND RELATED METHODS

(71) Applicant: FemtoDx, Inc., Beverly Hills, CA (US)

(72) Inventor: Pritiraj Mohanty, Beverly Hills, CA (US)

(73) Assignee: FemtoDx, Inc., Beverly Hills, CA (US)

(*) Notice: Subject to any disclaimer, the term of this patent is extended or adjusted under 35 U.S.C. 154(b) by 244 days.

(21) Appl. No.: 16/752,978

(22) Filed: Jan. 27, 2020

(65) Prior Publication Data

US 2020/0249198 A1  Aug. 6, 2020

Related U.S. Application Data

(60) Provisional application No. 62/799,183, filed on Jan. 31, 2019, provisional application No. 62/799,192, filed on Jan. 31, 2019, provisional application No. 62/799,203, filed on Jan. 31, 2019.

(51) Int. Cl.
| | |
|---|---|
| *G01N 27/414* | (2006.01) |
| *G01N 27/12* | (2006.01) |
| *G01N 27/403* | (2006.01) |
| *G01N 27/407* | (2006.01) |
| *G01N 27/327* | (2006.01) |
| *G01N 33/487* | (2006.01) |
| *G01F 1/684* | (2006.01) |
| *H01L 29/41* | (2006.01) |
| *H01L 29/417* | (2006.01) |
| *H01L 29/06* | (2006.01) |
| *B82Y 15/00* | (2011.01) |

(52) U.S. Cl.
CPC .......... *G01N 27/4146* (2013.01); *B82Y 15/00* (2013.01); *G01N 27/12* (2013.01); *G01N 27/3278* (2013.01); *G01N 27/4035* (2013.01); *G01N 27/4075* (2013.01); *G01N 33/48721* (2013.01); *H01L 29/413* (2013.01); *H01L 29/41766* (2013.01); *G01F 1/684* (2013.01); *H01L 29/0673* (2013.01)

(58) Field of Classification Search
CPC ............... G01N 27/4146; G01N 27/12; G01N 27/4035; G01N 27/4075; G01N 27/3278; G01N 33/48721; H01L 29/413; H01L 29/41766; H01L 29/0673; G01F 1/684; B82Y 15/00
See application file for complete search history.

(56) References Cited

U.S. PATENT DOCUMENTS

| | | | |
|---|---|---|---|
| 2015/0017740 A1* | 1/2015 | Shalev | G01N 33/54373 438/49 |
| 2016/0313278 A1* | 10/2016 | Knickerbocker | G01N 33/48721 |

\* cited by examiner

*Primary Examiner* — Melissa J Koval
*Assistant Examiner* — Joseph O Nyamogo
(74) *Attorney, Agent, or Firm* — Wolf, Greenfield & Sacks, P.C.

(57) ABSTRACT

The techniques relate to methods and apparatus for sensing an analyte. At least one sensor element is configured to sense an analyte, the at least one sensor element comprising a first portion and a second portion. A first current electrode is attached to the first portion and a second current electrode is attached to the second portion. A first measurement electrode is attached to the first portion and a second measurement electrode is attached to the second portion.

9 Claims, 20 Drawing Sheets

(A)

(B)

FOUR POINT SEMICONDUCTOR NANOWIRE-BASED SENSORS AND RELATED METHODS

RELATED APPLICATIONS

This application claims priority under 35 U.S.C. § 119(e) to U.S. Provisional Application Ser. No. 62/799,183, filed Jan. 31, 2019 and entitled "PROCESS FOR CREATING NANOWIRE FET BIOSENSORS WITH METALIZED CONTACTS," U.S. Provisional Application Ser. No. 62/799,192, filed Jan. 31, 2019 and entitled "SEMICONDUCTOR NANOWIRE-BASED SENSORS USING 4-POINT MEASUREMENT AND RELATED METHODS," and U.S. Provisional Application Ser. No. 62/799,203, filed Jan. 31, 2019 and entitled "NANOWIRE BIOSENSOR WITH INTEGRATED FLUID CONDUCTANCE MEASUREMENT AND RELATED METHODS," which are hereby incorporated by reference in their entirety.

FIELD

The techniques described herein relate generally to methods and apparatus for nanochannel-based sensors used to sense chemical or biological species, and in particular to four point semiconductor nanowire-based sensors and related methods.

BACKGROUND

Chemical or biological sensors can include nanowires and/or other small-scale electrical devices that essentially serve as sensitive transducers that convert chemical activity of interest into corresponding electrical signals that can be used to accurately represent the chemical activity. The nanosensors can include one or more nanowires (e.g., which may have a tubular form). The nanowires can be fabricated such that once functionalized, their surface will interact with adjacent molecular entities, such as chemical species. The interaction of the nanowires with molecular entities can induce a change in a property (such as conductance) of the nanowire.

SUMMARY

For many sensing applications, it can be beneficial to employ sensors having high sensitivity to a species of interest. Sensors with high sensitivity can be used to detect much smaller amounts or concentrations of the species, which may be necessary or desirable in some applications, and/or such sensors can provide a high signal-to-noise ratio and thus improve the quality of measurements that are taken using the sensor.

Some embodiments relate to a four-point measurement technique for measuring the voltage or conductance (or a change in voltage or conductance) of a nano sensor. As described herein, an array of semiconducting nanowires can be used as the active portion of sensors for biological molecules such as proteins, viruses, disease markers, and/or other organic compounds. The semiconducting nanowires can be attached through metallic electrodes to external electronics for measurement purposes. The performance of the device can be improved by using a four-point measurement technique and/or ion-implanted metal-to-semiconductor contacts. In some embodiments, two sets of electrodes are used, including one set for applying a voltage and a second set to measure a property of the sensor.

Some embodiments relate to a device that includes at least one sensor element configured to sense an analyte, the at least one sensor element comprising a first portion and a second portion, a first current electrode attached to the first portion and a second current electrode attached to the second portion, and a first measurement electrode attached to the first portion and a second measurement electrode attached to the second portion.

In some examples, the at least one sensor element comprises at least one semiconductor sensor in electrical communication with a source and a drain, the device further comprising a first contact pad in electrical communication with the source and a second contact pad in electrical communication with the drain. The first portion can be the first contact pad and the second portion can be the second contact pad, such that the first current electrode is attached to the first contact pad and the second current electrode attached to the second contact pad, and the first measurement electrode is attached to the first contact pad and the second measurement electrode is attached to the second contact pad. The first and second contact pads can include ion-implanted electrode attachment pads. The ions can include one or more Group III and/or Group V elements. The ions can include a metal.

In some examples, the source and drain comprise a semiconductor material. The first contact pad can include a first portion and a second portion different than the first portion, wherein the first portion overlaps the source, the second contact pad can include a first portion and a second portion different than the first portion, wherein the first portion overlaps the drain, and the first portions are ion-implanted and the second portions are not ion-implanted.

In some examples, the first current electrode is attached to a first portion of the first contact pad and the first measurement electrode is attached to a second portion of the first contact pad that is different than the first portion of the first contact pad, and the second current electrode is attached to a first portion of the second contact pad and the second measurement electrode is attached to a second portion of the second contact pad that is different than the first portion of the second contact pad.

In some examples, the source and drain each comprise a first portion proximate to the at least one semiconductor sensor and a second portion distal to the at least one semiconductor sensor, the first current electrode is attached to the second portion of the source and the second current electrode is attached to the second portion of the drain, and the first measurement electrode is attached to the first portion of the source and the second measurement electrode is attached to the first portion of the drain.

In some examples, the device includes a measurement device in electrical communication with the first measurement electrode and the second measurement electrode. The measurement device can include a voltmeter.

In some examples, a current source in electrical communication with the first current electrode and the second current electrode.

Some embodiments relate to a method for determining a conductance change of at least one sensor element to sense whether an analyte is present in a fluid. The method includes applying a current to a first current electrode attached to a first portion of the at least one sensor element and a second current electrode attached to a second portion of the at least one sensor element, measuring a voltage using a first measurement electrode attached to the first portion and a second measurement electrode attached to the second portion, and determining a conductance change of the at least one sensor element based on the measured voltage.

In some examples, determining the conductance change comprises determining a change in voltage.

Some embodiments relate to sensing the conductivity of a fluid. Biomolecular sensors can be based on any number of physical principles, and may generally depend on binding of a target molecule to a target receptor to induce a measurement change in the sensor. Many biomolecules and receptors have different binding characteristics that can depend on the ionic concentration of the surrounding fluid. The ionic concentration can, for example, influence the electrical conductivity of the fluid. The techniques described herein can be used to measure the conductance of a fluid. IN some embodiments, the techniques can integrate a conductance measuring mechanism with the biosensor, e.g., for purposes of characterizing the fluid simultaneously with biomolecular detection. The conductance can be used in conjunction with the changed property of the sensor to detect an analyte.

Some embodiments relate to a device comprising a fluid chamber, at least one sensor element configured to sense an analyte, wherein the at least one sensor element is in fluid communication with the fluid chamber, and a set of one or more electrodes in fluid communication with the fluid chamber for sensing a conductance of a fluid in the fluid chamber.

In some examples, the one or more electrodes comprise two electrodes in fluid communication with the fluid chamber. A voltage source can be in electrical communication with the two electrodes, and a measurement device can be in electrical communication with the two electrodes. The fluid chamber can be disposed over a first side of a substrate comprising the at least one sensor element. Each of the two electrodes can extend from a first area of the substrate within the fluid chamber to a second area of the substrate outside of the fluid chamber. Each of the two electrodes can include a thin film. Each of the two electrodes can include through silicon vias such that each of the two electrodes extends through the substrate to a second side of the substrate opposite the first side.

In some examples, the one or more electrodes can include four electrodes in fluid communication with the fluid chamber. A voltage source can be in electrical communication with a first two of the four electrodes, and a measurement device can be in electrical communication with a remaining two of the four electrodes. The fluid chamber can be disposed over a first side of a substrate comprising the at least one sensor element. Each of the four electrodes can extend from a first area of the substrate within the fluid chamber to a second area of the substrate outside of the fluid chamber. Each of the four electrodes can include a thin film. Each of the four electrodes can include through silicon vias such that each of the two electrodes extends through the substrate to a second side of the substrate opposite the first side.

In some examples, the one or more electrodes include a metal or a metal alloy.

In some examples, the one or more electrodes comprise insulating barrier covering a portion of the one or more electrodes in fluid communication with the fluid chamber.

Some embodiments relate to a method for determining a conductance of a fluid in a fluid chamber of a device comprising at least one sensor element configured to sense an analyte in the fluid, the method comprising applying a current using a set of one or more electrodes in fluid communication with the fluid in the fluid chamber, measuring a voltage using the set of one or more electrodes, and determining a conductance of the fluid based on the measured voltage.

In some examples, the set of one or more electrodes comprises two electrodes in fluid communication with the fluid chamber, applying the current comprises applying the current using the two electrodes, and measuring the voltage comprises measuring the voltage using the two electrodes.

In some examples, the set of one or more electrodes comprises four electrodes in fluid communication with the fluid chamber, applying the current comprises applying the current using a first two electrodes of the four electrodes, and measuring the voltage comprises measuring the voltage using a remaining two electrodes of the four electrodes.

In some examples, applying the current comprises applying an alternating current.

In some examples, applying the current comprises applying a direct current.

Some embodiments relate to sensing the conductivity and/or conductivity changes of a flowing fluid. Larger biomolecules, including those that may be too large to be detected using nanowire-based sensors, can be detected based on the conductance and/or changes in conductance as a fluid flows across a set of electrodes. The techniques described herein can be used to measure the conductance of a fluid as the fluid flows across one or more sets of electrodes that are spaced along a fluid chamber containing the fluid. The techniques can be used to detect an analyte, including those too large for detection using nanowire-based sensors. In some embodiments, the techniques can be combined with nanowire-based sensors to improve analyte detection.

Some embodiments relate to a device comprising a substrate, at least one set of a plurality of measurement electrodes disposed at least partially on a top surface of the substrate, and a fluid channel that extends along a direction such that a fluid introduced into the fluid channel flows along the direction, wherein the fluid channel is adjacent the top surface of the substrate, and the at least one set of the plurality of measurement electrodes are spaced along the direction of the fluid channel for determining a conductance of the fluid as the fluid flows through the fluid channel.

In some examples, the at least one set of the plurality of measurement electrodes comprises a first set of a plurality of measurement electrodes, and a second set of a plurality of measurement electrodes. The first set of the plurality of measurement electrodes can be approximately equally spaced along the direction and comprise a first fan-shaped array of measurement electrodes, the second set of the plurality of measurement electrodes can be approximately equally spaced along the direction and comprise a second fan-shaped array of measurement electrodes, and the first fan-shaped array of measurement electrodes is interlocked with the second fan-shaped array of measurement electrodes.

In some examples, the first fan-shaped array of measurement electrodes comprises a first backbone extending along the direction and spaced from the fluid channel on a first side of the fluid channel, and the second fan-shaped array of measurement electrodes comprises a second backbone extending along the direction and spaced from the fluid channel on a second side of the fluid channel.

In some examples, each measurement electrode of the first fan-shaped array of measurement electrodes comprises a first end in electrical communication with the first backbone and extends along a second direction substantially orthogonal to the first direction such that a second end of each of the measurement electrodes is disposed on the second side of the fluid channel, and each measurement electrode of the second fan-shaped array of measurement electrodes comprises a first end in electrical communication with the second backbone and extends along the second direction such that a second end of each of the measurement electrodes is disposed on the first side of the fluid channel.

In some examples, the device includes a first field adjustment electrode extending along the first direction, wherein the first field adjustment electrode is disposed on the first side and spaced further from the fluid channel than the first backbone, and a second field adjustment electrode extending along the first direction, wherein the second field adjustment electrode is disposed on the second side and spaced further from the fluid channel than the second backbone.

In some examples, the first set of the plurality of measurement electrodes each comprise approximately a same width. The second set of the plurality of measurement electrodes can each comprise approximately the same width.

In some examples, the device includes a set of field adjustment electrodes, wherein the set of field adjustment electrodes are on opposite sides of the fluid channel and spaced from the fluid channel.

In some examples, the device includes a voltage source in electrical communication with the at least one set of a plurality of measurement electrodes, and a measurement device in electrical communication with the at least one set of a plurality of measurement electrodes.

In some examples, the at least one set of a plurality of measurement electrodes comprise a metal or a metal alloy.

Some embodiments relate to a method for determining a conductance of a fluid flowing through a fluid channel of a device comprising at least one set of a plurality of measurement electrodes disposed at least partially on a top surface of a substrate, the method comprising administering a fluid into a fluid channel that extends along a direction so that the fluid flows along the direction, wherein the fluid channel is adjacent the top surface of the substrate and the at least one set of the plurality of measurement electrodes are spaced along the direction of the fluid channel, applying a current to the at least one set of a plurality of measurement electrodes, measuring a voltage using the set of one or more electrodes, and determining a conductance of the fluid flowing through the channel based on the measured voltage.

In some examples, applying the current comprises applying an alternating current.

In some examples, applying the current comprises applying a direct current.

In some examples, applying the current to the at least one set of the plurality of measurement electrodes comprises applying a current to a first set of a plurality of measurement electrodes, and a second set of a plurality of measurement electrodes.

In some examples, the method further comprises applying a voltage to a set of field adjustment electrodes, wherein the set of field adjustment electrodes are on opposite sides of the fluid channel and spaced from the fluid channel.

FIGURES

In the drawings, each identical or nearly identical component that is illustrated in various figures is represented by a like reference character. For purposes of clarity, not every component may be labeled in every drawing. The drawings are not necessarily drawn to scale, with emphasis instead being placed on illustrating various aspects of the techniques and devices described herein.

DETAILED DESCRIPTION

Nanochannel-based sensors can be used to detect an analyte in a liquid. The concentration of the analyte can be determined in a controlled environment based on various measurements, such as measurements taken of air, measurements taken using a blank liquid (without the analyte), and measurements taken using a test liquid that may (or may not) contain the analyte. Electrodes can be attached to the nanochannel-based sensors and used to sense characteristics of the sensors. However, the inventors have discovered and appreciated that when using a two-point measurement technique that uses the same electrodes to both apply a current and sense characteristics of the nano-channel based sensors (e.g., to sense the voltage or voltage change), the sensed characteristics may be subject to significant noise. For example, noise can be caused by induction loops in the circuitry, fluid regions in contact with the electrodes, thermal nose, and/or other sources of noise. The inventors have developed improvements to existing nanochannel-based sensing technologies that can be used to perform a four-point measurement technique that separates the electrodes used to apply the current from the electrodes used to sense the characteristic of the nanochannel. The measurement electrodes can be located proximate to the sensing components (e.g., nanowires) such that the measured property is only and/or largely determined based on the sensing component and not other components of the device. The pads and/or electrodes can be ion-implanted to achieve a strong connection with the nanochannel. The four-point measurement techniques can achieve better sensing capabilities than existing sensors by significantly reducing noise (e.g., compared to two-point techniques).

Large biomolecules, such as proteins or virus fragments (e.g., which can include nanoparticles, with size ranging from 10-5000 nm), can be considered dielectric nanoparticles. In some embodiments, the biomolecules are naturally uncharged. In certain embodiments, the biomolecules are charged, and attract free ions in solution to become effectively neutral. In such embodiments, the size of the dielectric particle is increased from the size of the bare particle by the Debye length, e.g., typically on the order of 1-10 nm.

Figure 1A:
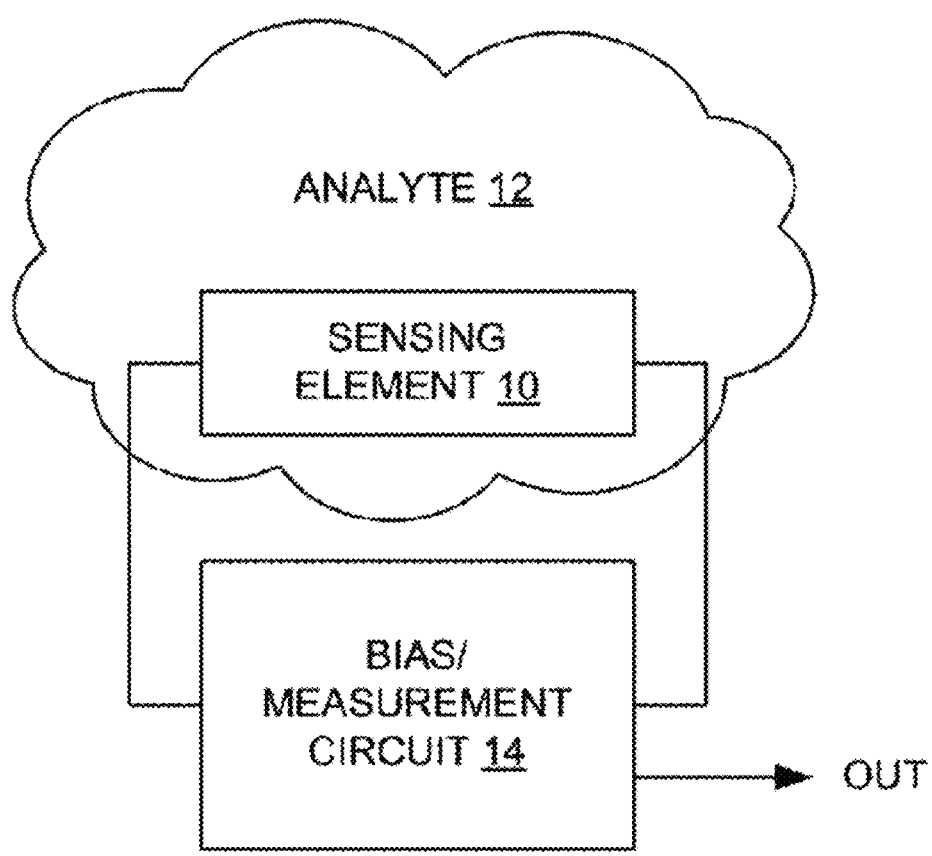
FIG. 1A is a schematic diagram illustrating the use of a sensor device used to detect species in an analyte solution, according to some examples.

Various types of molecular sensors, such as field effect biomolecule sensors (e.g., nanowire field effect transistors), can be used to detect biomolecules of interest. In FIG. 1A, a sensing element 10 is exposed to chemical or biological species (analyte) in an analyte solution 12. The sensing element 10 has connections to a bias/measurement circuit 14 that provides a bias voltage to the sensing element 10 and measures the differential conductance of the sensing element 10 (e.g., the small-signal change of conductance with respect to bias voltage). The differential conductance of the device is measured by applying a small modulation of bias voltage to generate a value of an output signal (OUT) that provides information about the chemical or biological species of interest in the analyte solution 12, for example a simple presence/absence indication or a multi-valued indication representing a concentration of the species in the analyte solution 12.

Suitable sensing elements (e.g., including semiconductor nanowires) and sensing technologies have been described in commonly-owned International Publication Number WO 2016/089,453, U.S. Pat. No. 10,378,044 and U.S. Publication No. 2014/0030747, each of which are incorporated herein by reference in their entireties.

The sensing element 12 includes one or more elongated conductors of a semiconductor material such as silicon, which may be doped with impurities to achieve desired electrical characteristics. The dimensions of a channel can be sufficiently small (e.g., nanoscale) such that chemical/electrical activity on the channel surface can have a much more pronounced effect on electrical operation than in larger devices. Such nanoscale channels may be referred to as nanochannels herein. In some embodiments, the sensing element 12 has one or more constituent nanochannels having a cross-sectional dimension of less than about 150 nm (nanometers), and even more preferably less than about 100 nm.

As described herein, the surface of the sensing element 12 can be functionalized by using a series of chemical reactions to incorporate receptors or sites for chemical interaction with the species of interest in the analyte solution 12. As a result of this interaction, the charge distribution, or surface potential, of the surface of the sensing element 12 changes in a corresponding manner. Such a change of surface potential can alter the conductivity of the sensing element 10 in a way that is detected and measured by the bias/measurement circuit 14. Thus, the sensing element 12 can operate as a field-effect device, since the channel conductivity can be affected by a localized electric field related to the surface potential or surface charge density. The measured differential conductance values can be converted into values representing the property of interest (e.g., the presence or concentration of species), based on known relationships as may have been established in a separate calibration procedure, for example.

Figure 1B:
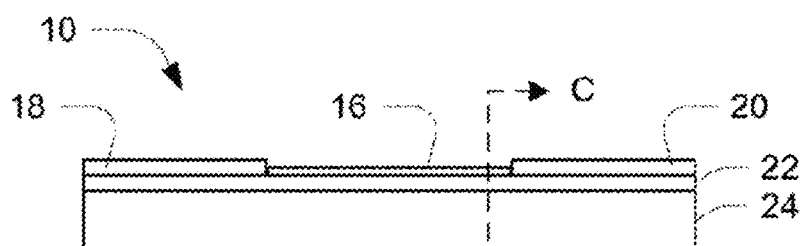
FIG. 1B-1E depict a nanochannel-based sensing element that can be used in the circuit of FIG. 1A, according to some examples.
Figure 1D:
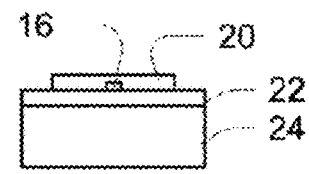
Figure 1C:
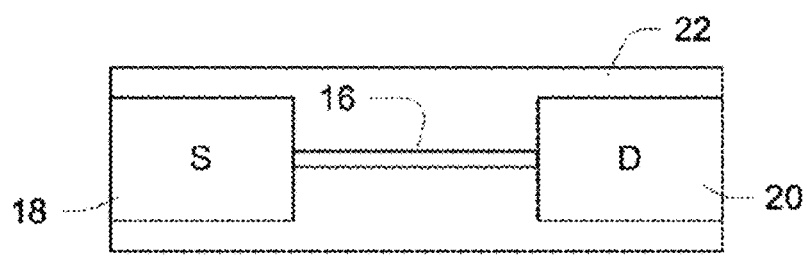
Figure 1E:
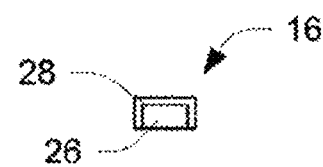

FIGS. 1B-1E shows a sensing element 10 according to one example. As shown in FIG. 1B, a silicon nanochannel 16 extends between a source (S) contact 18 and a drain (D) contact 20, all formed on an insulating oxide layer 22 above a silicon substrate 24. FIG. 1C is a top view showing the narrow elongated nanochannel 16 extending between the wider source and drain contacts 18, 20, which are formed of a conductive material such as gold-plated titanium for example. FIG. 1D shows the cross-sectional view in the plane C-C of FIG. 1B. FIG. 1E shows the cross section of the nanochannel 16 in more detail. In the illustrated embodiment, the nanochannel 16 includes an inner silicon member 26 and an outer oxide layer 28 such as aluminum oxide.

Figure 1F:
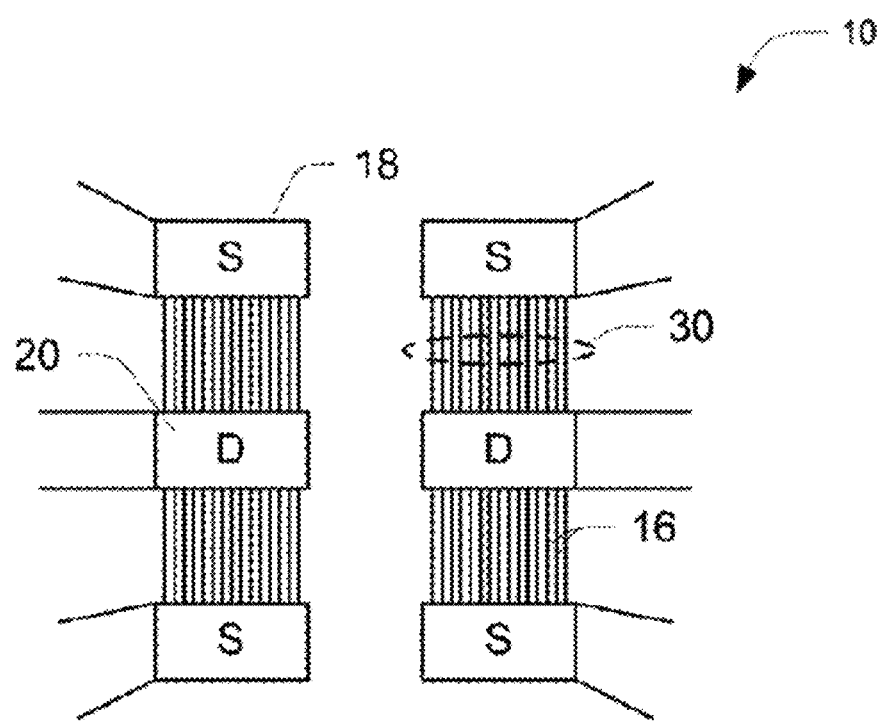
FIG. 1F depicts a sensor employing an array of nanochannels, according to some examples.

FIG. 1F shows a sensing element 10 employing an array of nanochannels 16, which in the illustrated example are arranged into four sets 30, each set including approximately twenty parallel nanochannels 16 extending between respective source and drain contacts 18, 20. By utilizing arrays of nanochannels 16 such as shown, greater signal strength (current) can be obtained, which can improve the signal-to-noise ratio of the sensing element 10. To obtain fully parallel operation, the source contacts 18 are all connected together by separate electrical conductors, and likewise the drain contacts 20 are connected together by separate electrical conductors. Other configurations are of course possible. For example, each set 30 may be functionalized differently so as to react to different species which may be present in the analyte solution 12, enabling an assay-like operation. In such configurations, it should be understood that each set 30 has separate connections to the bias/measurement circuit 14 to provide for independent operation.

The sensing element 10 may be made by a variety of techniques employing generally known semiconductor manufacturing equipment and methods. In some embodiments, Silicon-on-Insulator (SOI) wafers are employed. A starting SOI wafer may have a device layer thickness of 100 nm and oxide layer thickness of 380 nm, on a 600 µm boron-doped substrate, with a device-layer volume resistivity of 10-20 Ω-cm. After patterning the nanochannel channels and the electrodes (e.g., in separate steps), the structure can be etched out with an anisotropic reactive-ion etch (RIE). This process can expose the three surfaces (top and sides) of the silicon nanochannels 16 along the longitudinal direction, resulting in increased surface-to-volume ratio. A layer of $Al_2O_3$ (e.g., approximately 5 to 15 nm thick) can be grown using atomic layer deposition (ALD). Selective response to specific biological or chemical species can be realized by fabricating the nanochannels 16 such that once functionalized, the nanochannels 16 react to one or more analytes. In use, a flow cell, such as a machined plastic flow cell, can be employed. For example, a machined plastic flow cell can be fitted to the device and sealed with silicone gel, with the sensing element 10 bathed in a fluid volume (of about 30 µL for example), connected to a syringe pump.

In some embodiments, the sensing element 10 may include other control elements or gates adjacent to the nanochannels 16. For example, the sensing element 10 can include a top gate, which can be a conductive element formed along the top of each nanochannel 16. Such a top gate may be useful for testing, characterization, and/or in some applications during use, to provide a way to tune the conductance of the sensing element in a desired manner. As another example, the sensing element 10 may include one or more side gates formed alongside each nanochannel 16 immediately adjacent to the oxide layer 28, which can be used for similar purposes as a top gate. As a further example, in some embodiments the sensing element 10 can include a temperature sensor (e.g., disposed near the nanochannels). The system can use measurements from the temperature sensor to modify the system operations. For example, the circuitry can be configured to adjust how the system maps measured nanowire conductances to the concentration of an analyte.

Such molecular detection, where the presence of a specific molecule can be determined, can be useful for a variety of applications, including cancer detection, disease verification, and other medical and biological applications. In some embodiments, the sensor component consists of a binding molecule attached to the surface of a semiconducting material (e.g., functionalized on the surface). In some embodiments, the semiconductor is patterned into nanowires. In some embodiments, the semiconductor material is silicon, germanium, a III-V semiconductor, and/or the like. The binding molecules, which can also be referred to as detectors, can be designed to be particle-specific, such that only one specific particle (the analyte) will bind to a given detector. In some embodiments, the detector is an antibody. In some embodiments, the detector is a DNA or RNA fragment. In some embodiments, the analyte is a protein. In some embodiments, the analyte is a virus particle. It should be appreciated that the techniques described herein can be used in conjunction with any possible detector and analyte species combinations.

Figure 1G:
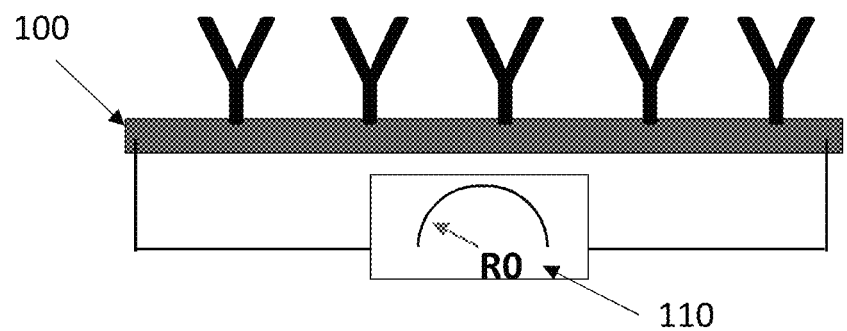
FIGS. 1G-1H are exemplary schematic diagrams of a semiconductor-based biomolecular analyte sensor, according to some examples.
Figure 1H:
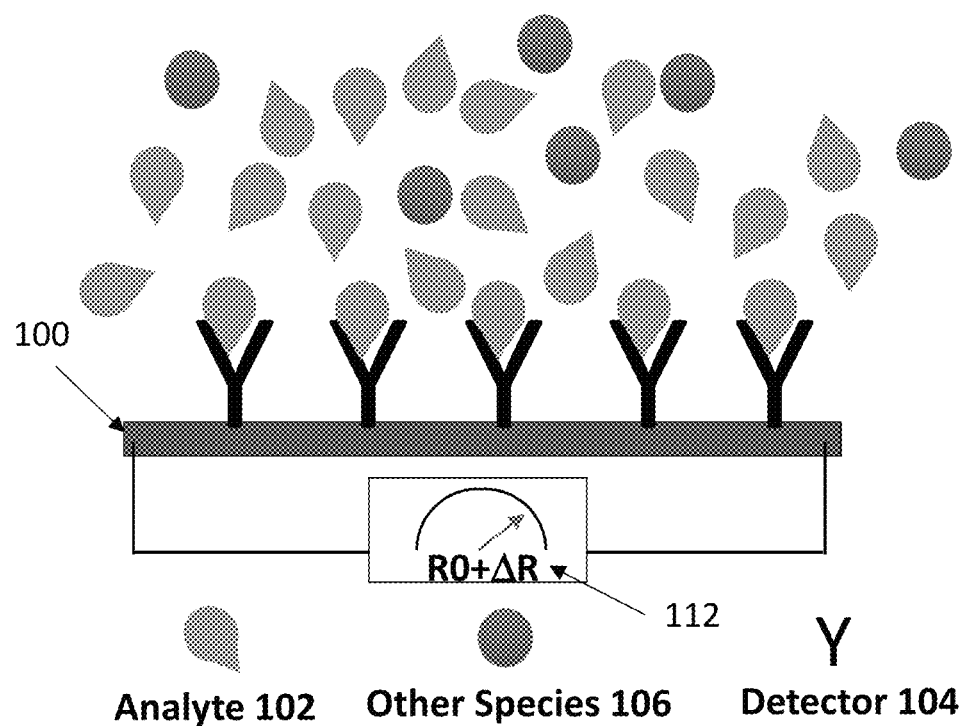

FIGS. 1G-1H are schematic diagrams of a general semiconductor-based biomolecular analyte sensor, according to some embodiments. As shown in FIG. 1H, binding of the specific analyte 102 to the detector molecule 104 results in a change in resistance of the semiconductor 100 relative to the bare state, as shown in FIG. 1G. When the analyte 102 binds to the detector, it is held close to the substrate and no longer migrates within the fluid containing the analyte and other species 106. The binding of the analyte 102 causes a measurable change in physical properties of the semiconductor 100. In some embodiments, a measured resistance (or conductance) change $\Delta R$ (or $\Delta G$) indicates the presence of the analyte, as illustrated in FIG. 1G (showing R0 110) and 1H (showing R0+$\Delta R$ 112). In some embodiments, the analyte charge causes the change in conductivity. In some embodiments, structural changes in the detector molecule 104 upon binding cause the measurable changes. In some embodiments, the change is due to electrical gating by the analyte 102. In some embodiments, the change is due to a change in the surface plasmon resonance. In some embodiments, the conductance change can be generally detected electrically by applying an electric current to the sensor and measuring a change in voltage. The application of currents and measuring of voltages can be performed using metal electrodes that attach to the semiconductor sensor, as described further herein.

Figure 2:
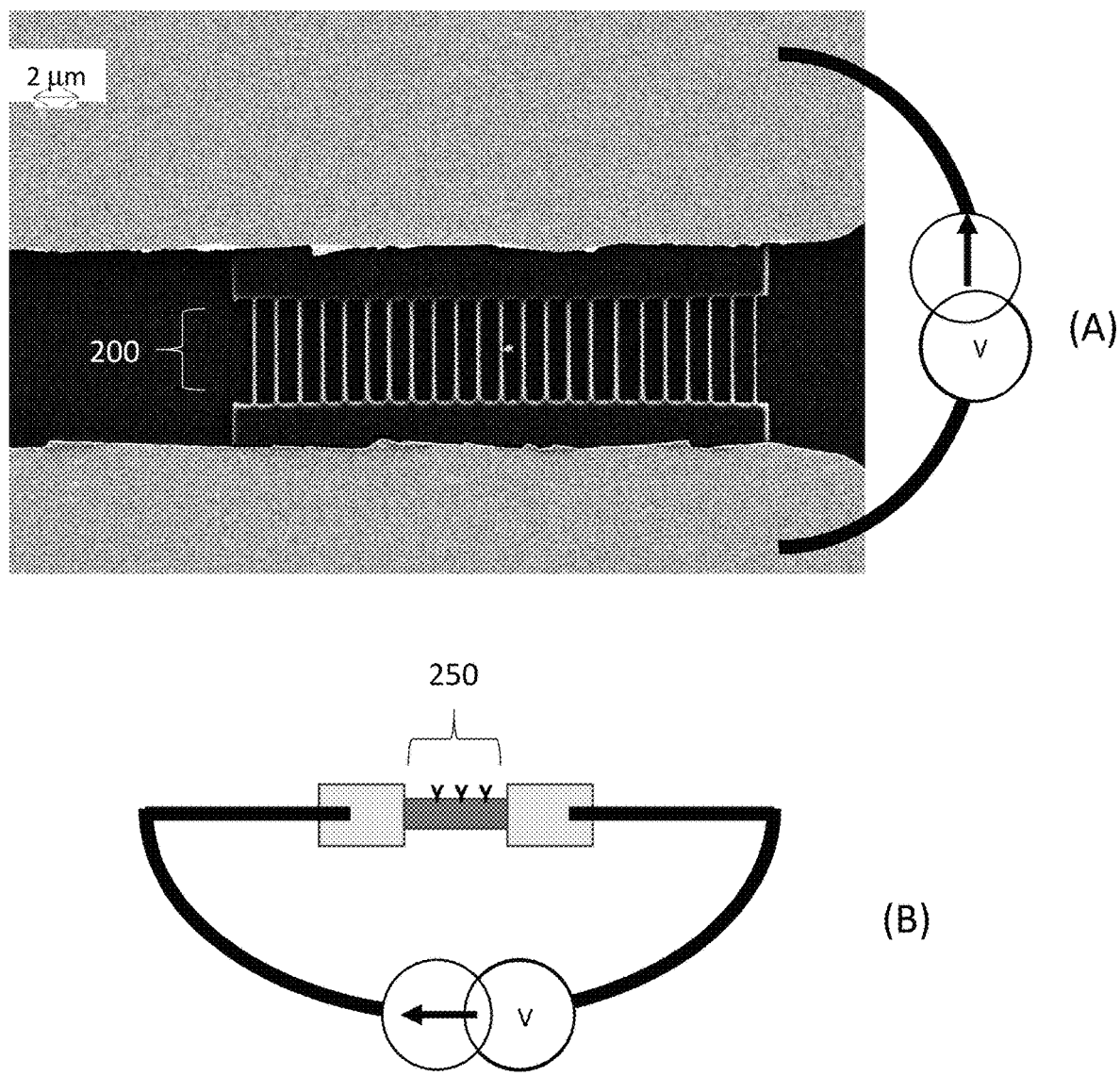
FIG. 2A is an exemplary diagram of a 2-point resistance measurement biosensor with one set of electrodes attached to the semiconductor sensor region, according to some examples.
FIG. 2B is an exemplary schematic illustration of a 2-point resistance measurement biosensor with one set of electrodes attached to the semiconductor sensor region, according to some examples.

A challenge to biosensor development can include signal noise when measuring properties of the sensor. The sensor can be connected to external measurement devices such as ohmmeters, voltmeters, and ammeters, for the purposes of detecting electrical properties or changes in electrical properties (e.g., resistance changes). The sensor is typically disposed in the middle of a large fluid volume, while connections are made outside of the fluid, which can result in very long electrodes, cables, and other circuitry. Some sensor geometries utilize a two-point measurement technique, where the measurement circuit consists of a single loop including the sensor and any wires, cable, and electrodes. A constant current is applied to the sample, and the resistance of the entire circuit is obtained by determining how much voltage is necessary to sustain that current, in accordance with Ohm's Law, as illustrated in FIG. 2A for an actual device and FIG. 2B a schematic. FIG. 2A is a diagram of a 2-point resistance measurement biosensor with one set of electrodes attached to the pure semiconductor sensor region, according to some examples, and FIG. 2B is a schematic illustration of the diagram in FIG. 2A. The nanowire region 200, 250 between the electrodes is the same semiconductor material as the electrode attachment region, with contacts that are typically highly resistive and non-ohmic.

The measured voltage using a 2-point resistance measurement is that across the entire circuit. In some embodiments, the electrodes and wires are metal, can be quite long and thin, and may suffer from very large contact resistance when deposited on pure silicon. Some or all of these factors can contribute to significant noise and background in measurements. Noise may be related to, for example, induction loops in the circuitry, noise generated by the fluid in regions where the electrodes are in contact with the fluid, thermal noise, and/or other sources. This noise, which can depend roughly on the total length of the circuit and quality of all contacts, can be much larger than any resistance change induced by analyte binding (e.g., as discussed in conjunctions FIGS. 1G-1H). Therefore, it can be highly desirable to reduce and/or eliminate such systematic noise from a measurement for enhanced biosensors.

Figure 3:
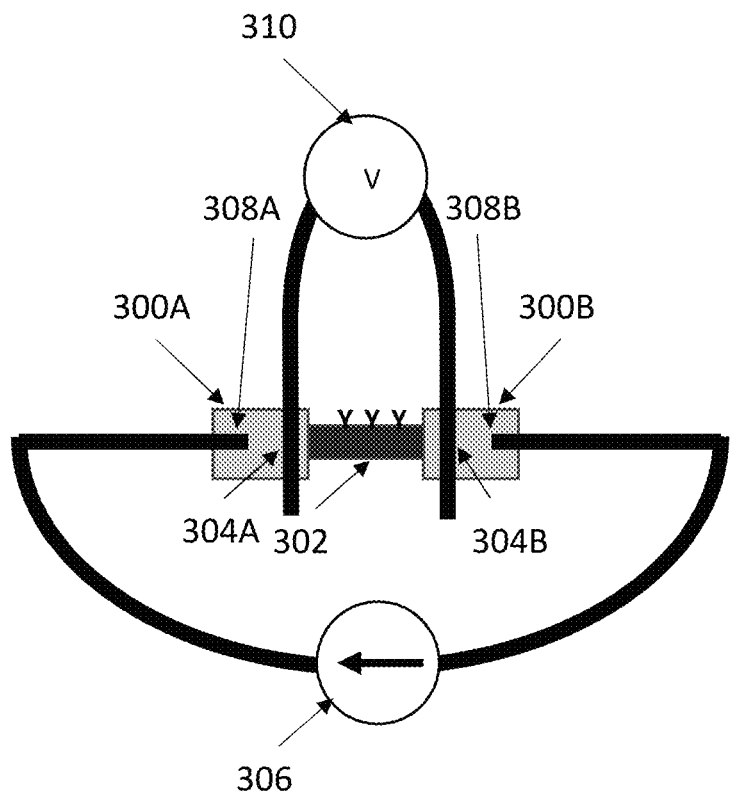
FIG. 3 is an exemplary schematic diagram of a 4-point measurement biosensor with ion-implanted contact regions, according to some embodiments.

The techniques described herein provide for reducing the measurement noise by using a four-point resistance probe with ion-implanted ohmic electrode contacts, illustrated schematically in FIG. 3. The basic components are the functionalized region 302 (e.g., which can include functionalized semiconductor nanowires), ion-implanted (e.g., metalized) semiconductor electrode attachment pads 300A, 300B (collectively referred to herein as electrode connection pads 300), current electrodes 308A, 308B (collectively referred to herein as current electrodes 308), current source 306, voltage measurement electrodes 304A, 304B (collectively referred to herein as voltage measurement electrodes 304), and a measurement device, such as a voltmeter 310. The electrode connection pads 300 can be ion-implanted, which can create very low resistance, ohmic contacts to the metal electrodes 304, 308, while the functionalized detection region 302 is semiconducting. The measured electrical property (e.g., voltage) is largely and/or solely that between the voltage measurement electrodes 304, which is only across the functionalized region 302. As shown in FIG. 3, in some embodiments the current electrodes 308 are attached to portions of the contact pads 300 that are located away from the functionalized region 302, and the measurement electrodes 304 are attached to portions of the contact pads that are proximate to the functionalized region 302.

The ion-implanted pads 300 can achieve good electrical continuity and/or low resistance from the electrodes 304, 308 to the semiconducting nanowires in the functionalized region 302. Ordinary semiconductor-metal contacts can be highly resistive, which limits the voltmeter sensitivity if the contact resistance is of the same order as the current-limiting resistor in the voltmeter. Ordinary semiconductor-metal contacts may also be nonohmic, and provide nonlinear background resistances as a function of applied current, which can limit measurement accuracy. In some embodiments, implanted ions are group III or group V elements, which are n- or p-type dopants, such as B, P, and As. In some embodiments, the implanted ions are metals such as Al or Ti. It should be appreciated that the techniques described herein address general ion-implanted connector pads utilizing any material that can be used to cause the semiconductor to become highly conductive or metallic in the ion-implanted region. In some embodiments, the ions are implanted only in the region where any given embodiment's design has overlap between the electrode and the semiconductor (e.g., and nowhere else). In some embodiments this is accomplished through microlithography or nanolithography. In some embodiments, ions are implanted through gas-phase exposure and annealing. In some embodiments, ions are implanted through surface deposition and annealing. In some embodiments, the electrodes are deposited on pristine semiconductor and annealed to create the ion implanted regions. While some examples of techniques for ion implanting are described, the techniques can be used with any and all methods of ion implanting (e.g., including in the region where the electrodes contact the semiconductor and/or other regions, such as the entire pad).

Figure 4A:
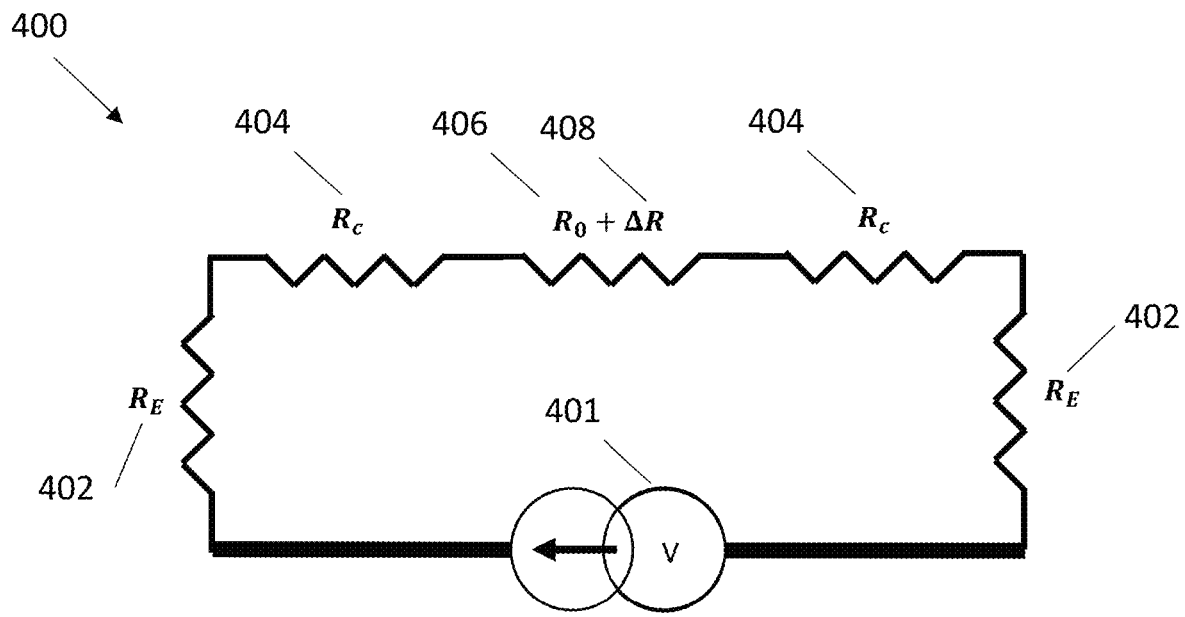
FIG. 4A is an exemplary circuit diagram for two-point measurement, according to some examples.

FIG. 4A shows a circuit 400 for two-point measurement, according to some examples. The measured voltage 401 across the circuit 400 for a given input current is equal to $V=I*(2*R_E+2*R_C+R_0+\Delta R)$, where $R_E$ 402 is the resistance of the electrodes plus circuitry, $R_C$ 404 is the contact resistance between the electrode and semiconductor, $R_0$ 406 is the bare resistance of the nanowires, and $\Delta R$ 408 is the resistance change due to analyte binding. For exemplary purposes, this considers symmetric contacts and electrodes, but this may not be the case in a real device. The techniques may be generalized to asymmetric contact and electrode resistances.

Each equivalent resistor contains noise, $\delta R\_i$, and the contact resistance without ion implantation may not be ohmic, such that $R_C$ is effectively a function of applied current. The signal may then consist of a constant background, $Vb=I*(2*R_E+2*R_C(I)+R_0)$, plus noise $Vn=I*\Sigma\_i \, \delta R\_i$. This noise may be significantly larger than the change in signal due to analyte binding, $Vs=I*\Delta R$. The effective noise can additionally or alternatively be enhanced due to the nonohmic nature of the contacts. Additionally, the background voltage, which includes the electrode and contact resistances, may be large, so that the fractional resistance change $\Delta R/(2*R_E+2*R_C+R_0)$ is unmeasurable.

Figure 4B:
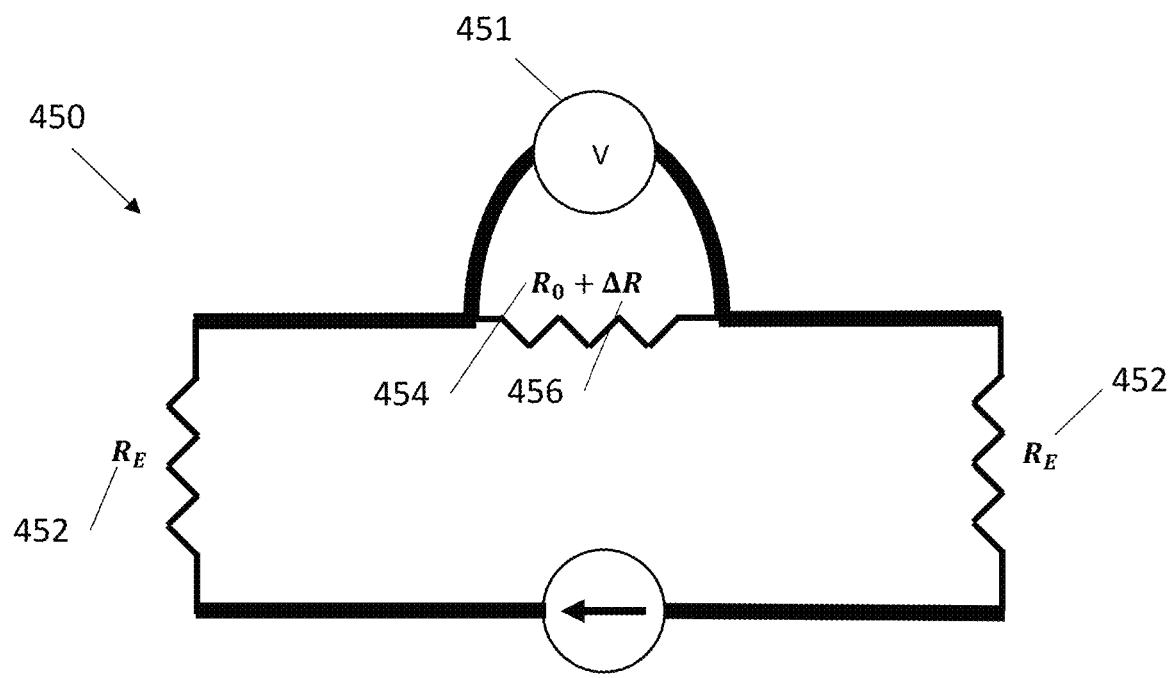
FIG. 4B is an exemplary circuit diagram for 4-point measurement with ion-implanted contacts, according to some embodiments.
Figure 5:
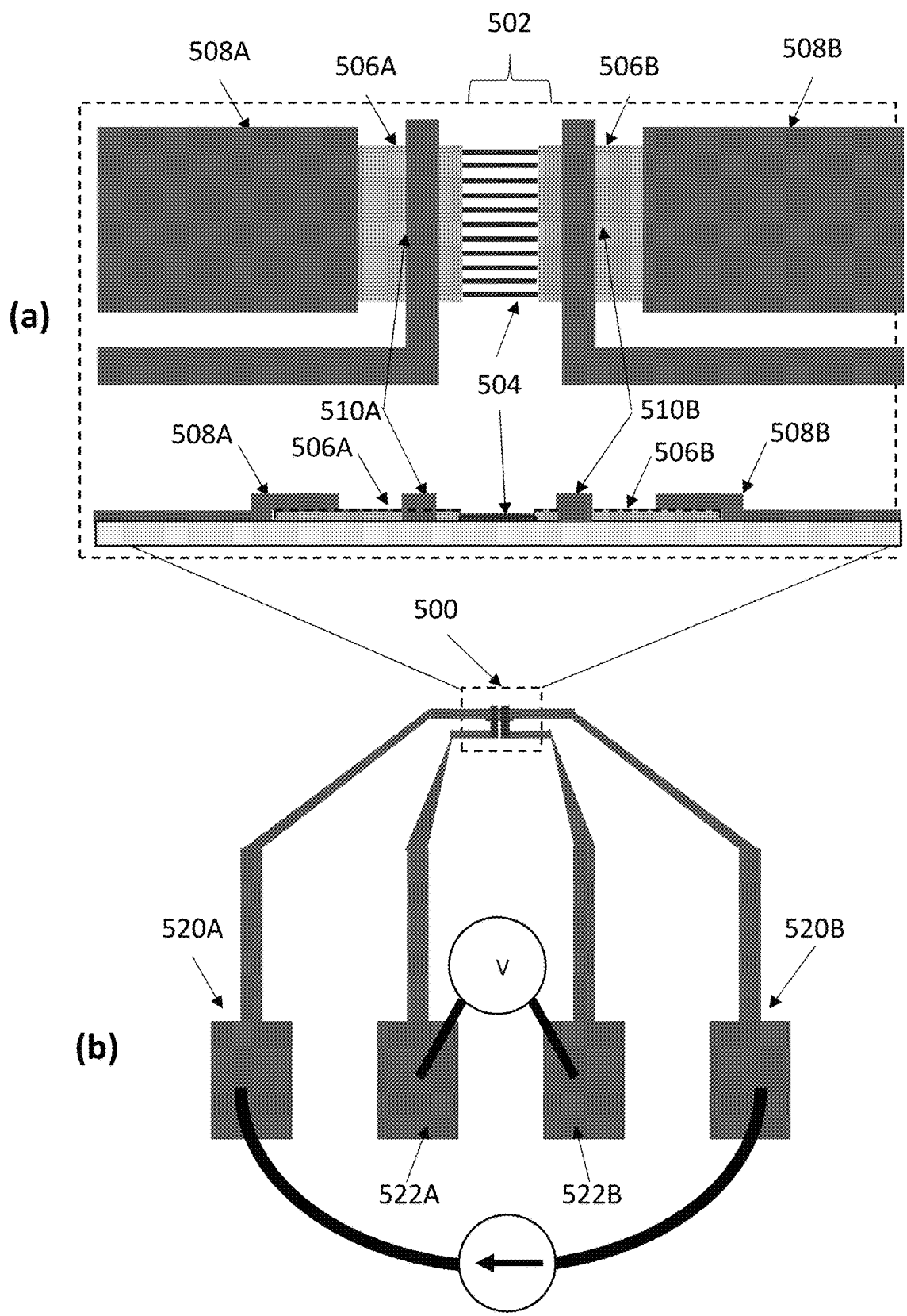
FIG. 5 is a schematic diagram of a circuit configured for 4-point measurement, according to some embodiments.

In the four-point techniques described herein, a constant current I can be applied to the circuit and the voltage mostly/only across the sensor region is measured. As described herein, to achieve a four-point measurement, two voltage detection electrodes are used (e.g., added to the two-point sensor geometry) that are separate from the voltage electrodes. The voltage detection electrodes can be placed as close as possible to the nanowire sensor region edges. FIG. 4B shows an exemplary circuit 450 for four-point measurement, with negligible contact resistance between the electrode and the ion-implanted semiconductor, according to some embodiments. The voltage V 451 is measured through a very high impedance circuit, which can reduce and/or eliminate currents (and associated noise) generated in the voltage measurement electrodes. FIG. 4B shows $R_E$ 452, $R_0$ 454 and $\Delta R$ 456. The measured voltage difference $V=I*(R_0+\Delta R)$ then measures only the voltage drop, and hence the resistance, across the sensor region. The noise sources in the electrodes and current contacts are thus eliminated from the measured signal, and the signal quality can improve (dramatically, in some cases). Analyte binding is then sensed by measuring the change in voltage $\Delta V=\Delta R*I$ relative to the background $Vb=I*R_0$. In some embodiments, the background may be subtracted out, or measurements performed relative to the background, further increasing sensitivity FIG. 5 is an exemplary schematic of a biosensor configured for 4-point measurement, according to some embodiments. A close-up of the sensor region 500 is shown in section (a), including a top view and a side view, which includes the sensor 502 (e.g., including in this examples semiconducting nanowires 504 connected to ion-implanted semiconductor pads 506A, 506B); the current electrodes 508A, 508B; and the voltage measurement electrodes 510A, 510B. In some embodiments, one or more of the sets of electrodes are coated with an insulating layer, including but not limited to, $Al_2O_3$, $SiO_2$, $HfO_2$, or $Si_3N_4$. Section (b) shows the sensor integrated into a microchip, including the metal electrode pads 520A, 520B connected to the current electrodes 508A, 508B, respectively, and metal electrode pads 522A, 522B that connect to the voltage electrodes 510A, 510B, respectively. The metal electrode pads can be used to connect to external circuitry. It should be appreciated that the configuration shown in FIG. 5 is for exemplary purposes only, as embodiments can have different bonding pad configurations and/or different electrode configurations. The techniques described herein can be integrated with other biosensor techniques, such as electroosmotic and electrophoretic flow techniques.

Some embodiments relate to a semiconductor fabrication process for fabricating a biosensor (e.g., a nanowire FET biosensor) according to some embodiments of the techniques described herein. In summary, starting materials for the biosensor fabrication can include a doped semiconductor on top of a buried oxide layer. An example of such a doped semiconductor is a silicon-on-insulator (SOI), which consists of a silicon layer on top of a silicon oxide layer, and optionally also on a thick buried silicon layer. In some embodiments, the semiconductor is a group IV element such as Si or Ge. In some embodiments, the semiconductor is a III-V alloy or II-IV alloy such as GaAs, InAs, InP, GaP, ZnSe, or ZnS. These are examples and are not intended to be limiting.

FIGS. 6-11 describe an exemplary sensor made from a thin silicon layer (e.g., around 100 nm thick, 50 nm thick, and/or other thicknesses), which is on top of a silicon dioxide layer (e.g., 200 nm thick, 300 nm thick, and/or other thicknesses). It should be appreciated that the techniques described herein are not limited in terms of the thickness(es) of the semiconductor on top of insulator. The sensor in this exemplary embodiment includes functionalized nanowires connected through a metalized semiconductor region to metal electrodes, which can then be attached to measurement equipment. The sensor can be used to detect biological molecules through resistance or conductance changes when a given analyte molecule binds to one of a number of receptor molecules, which are functionalized onto the nanowire. In some embodiments, the finished device may take on one of many equivalent geometries. Multiple geometries may be made on a single wafer using advanced manufacturing processes.

Figure 6:
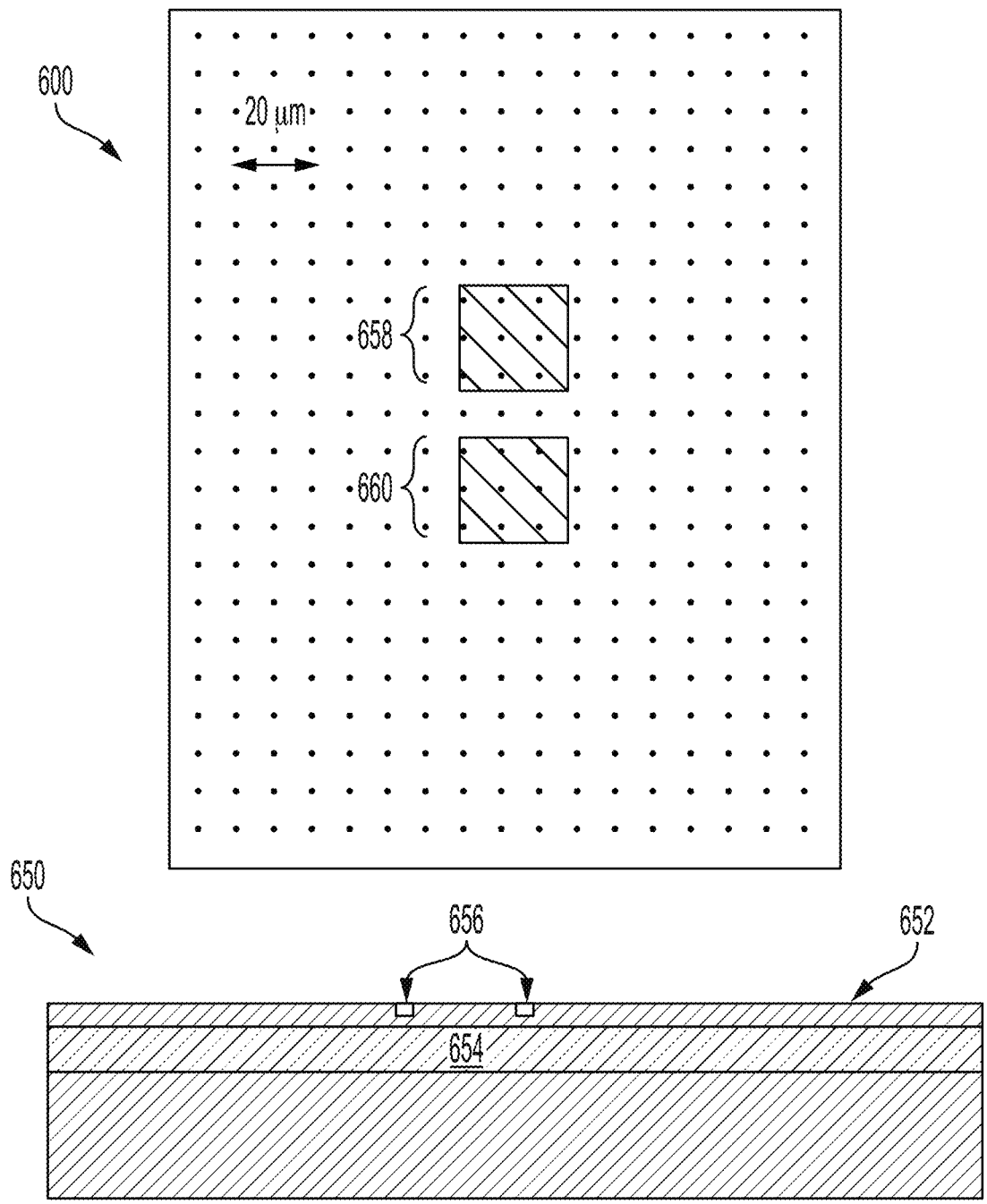
FIG. 6 is an exemplary diagram of a pattern for metallization and a corresponding side-view of the structure of a silicon on insulator structure with metalized regions, according to some embodiments.

FIG. 6 shows a diagram 600 of the pattern for metallization, according to some embodiments. The schematic side-view of structure 650 shows a representative silicon 652 on insulator 654 structure with metalized regions 656. The semiconductor is metalized by implanting ions in the regions 658, 660 where the metal electrode connections are to be made, representing an exemplary geometrical embodiment not intended to be limiting. The ions can be metals and/or other dopants. In some embodiments, metallization is achieved through ion implantation. In these embodiments, the ions are a group III or group V atom such as B or P. Ion implantation involves bombardment of the semiconductor with a gas-phase ion-containing compound followed by a high-temperature anneal. In some embodiments, metallization is achieved through doping with a metal. In such embodiments, the dopant is a metal. Metal doping can be achieved through surface deposition and high temperature annealing. Some embodiments may use other metallization techniques, and can be used with any such technique.

Figure 7:
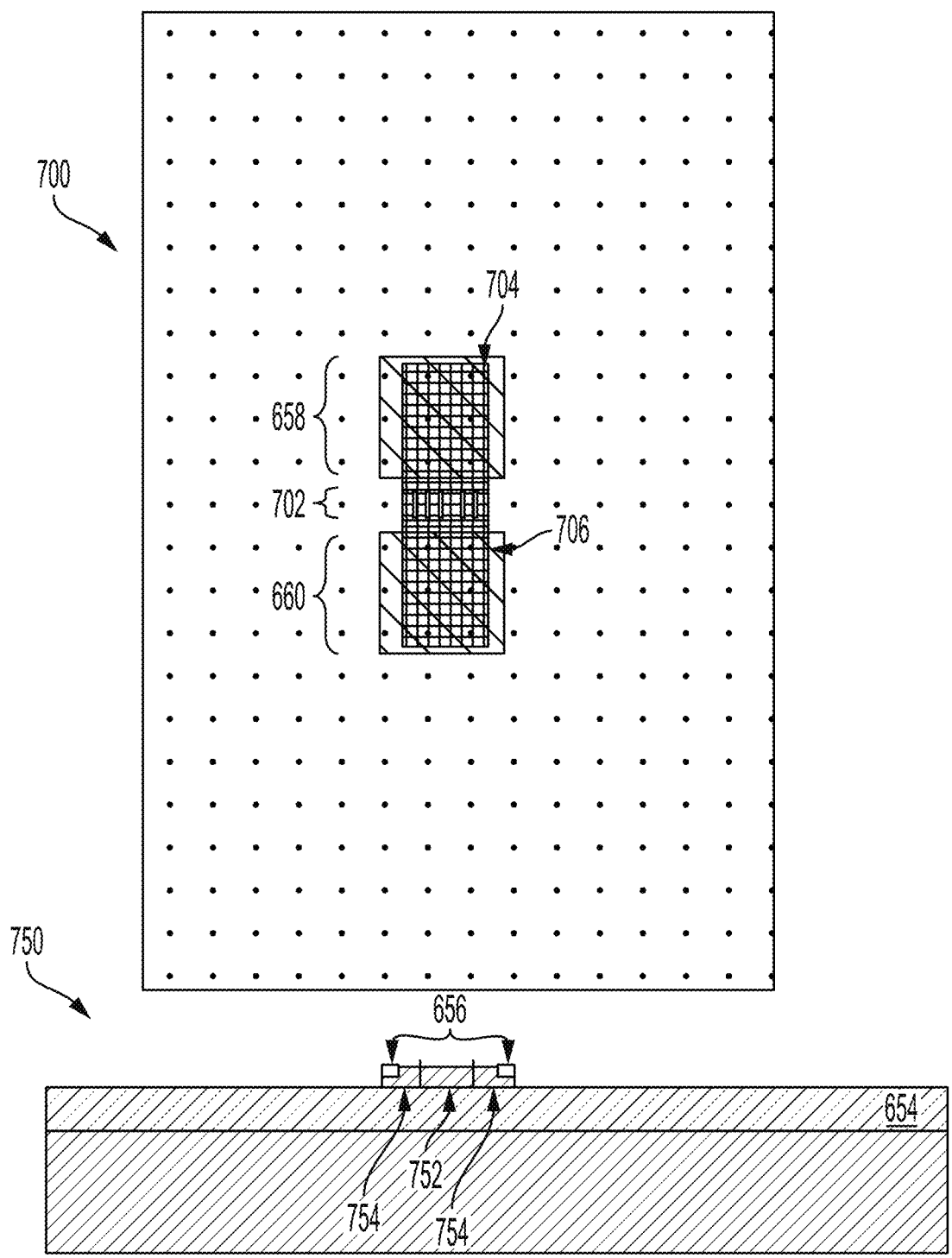
FIG. 7 is an exemplary diagram of a pattern for nanowires and connection pads overlaid on the metalized region, and a corresponding side-view of the structure of FIG. 6 after etching to define the nanowire and pads structure, according to some embodiments.

FIG. 7 shows an exemplary diagram 700 of the pattern for the nanowires 702 and connection pads 704, 706 overlaid on the metalized regions 658 and 660, respectively, according to some embodiments. The schematic side view of the structure 750 shows the structure 650 from FIG. 6 after etching to define the nanowire and pads structure. Vertical lines 756 demarcate the nanowire region 752 and pad region 754. In some embodiments, the nanowires and electrode attachment pads are created by electron beam lithography and reactive ion etching, which removes silicon 652 shown in FIG. 6 everywhere except the sensor region. In some embodiments, the nanowires are defined with photolithography. In some embodiments, the nanowires and pads are defined in multiple separate lithography steps. These and other techniques can be used to define the nanowire structures. After lithography has defined the nanowire 702 and pad 704/706 features, a hard mask can be deposited and any photolithography and electron beam resist is removed. In some embodiments, the hard mask is a metal. In some embodiments, the hard mask is an oxide. The hard mask allows the semiconductor etchant to be used and not etch the hard mask material, and vice versa. After the hard mask is deposited, the semiconductor is etched, leaving the nanowire and pad pattern as shown in 750.

Figure 8:
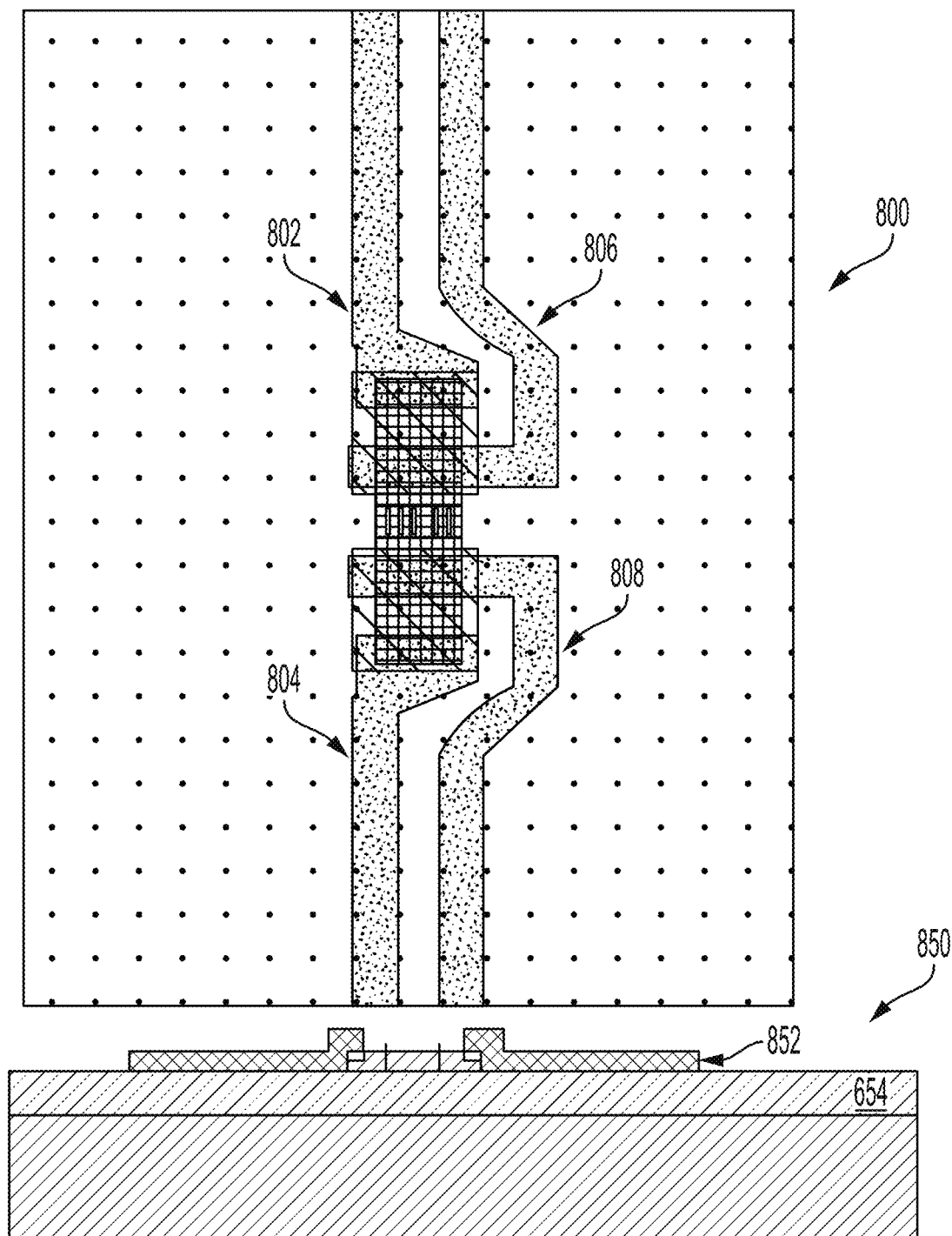
FIG. 8 is an exemplary diagram of electrodes overlaid on the nanowires and pads, and a corresponding side-view of the structure of FIG. 7 with the metal electrodes deposited, according to some embodiments.
Figure 10:
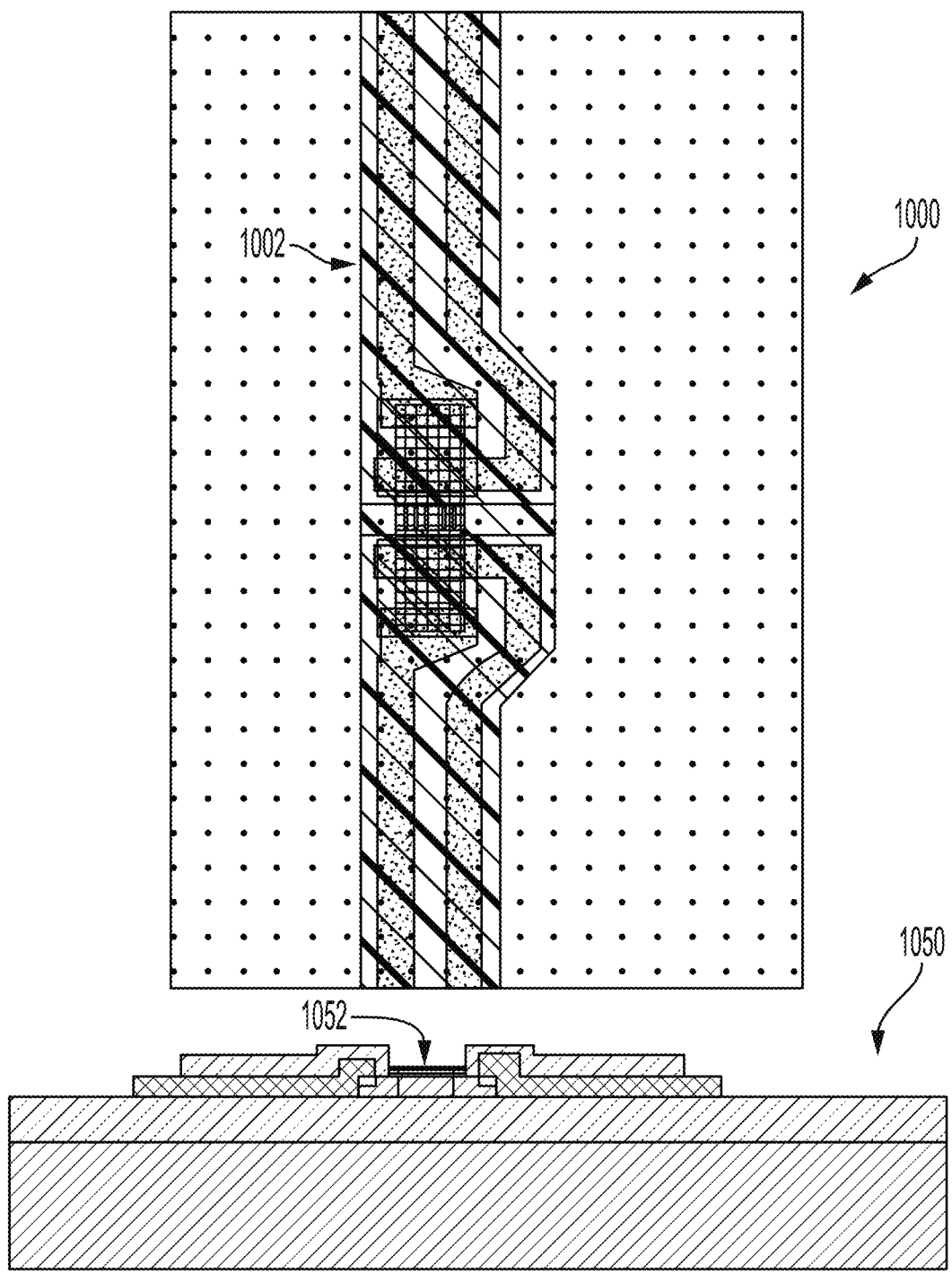
FIG. 10 is an exemplary diagram of a second insulating layer (e.g., a thin insulating layer) overlaid on the nanowires, pads, electrodes, and insulating layer, and a corresponding side-view of the structure of FIG. 9 with the second insulating layer deposited, according to some embodiments.

FIG. 8 shows an exemplary diagram 800 of electrodes overlaid on the nanowires and pads, according to some embodiments. The schematic side-view of the structure 850 shows the metal electrodes 852 deposited on the structure 750 from FIG. 7. FIG. 8 shows a representative 4-point measurement electrode pattern, with electrodes 802 and 804 being voltage electrodes and electrodes 806 and 808 being measurement electrodes. It should be appreciated that other geometries can be used, such as a two-electrode geometry for a two-point resistance measurement. Some embodiments may use three, four, or more electrodes for differential, four-point, and/or other measurement techniques. The pattern for the metal electrodes can be created with photolithography and the metal electrodes are deposited. The electrodes can be a metal, such as Au, Cu, Ag, Al, and may be an alloy or metallic multilayer. In some embodiments, an adhesion layer of Ti, Ta, or another metal can be used. The electrodes are approximately 10 to 20 microns wide near the sensor and become wider farther away (e.g., as shown in FIG. 10). In some embodiments, the metal thickness is in the range of 50 nm, 100 nm, 150 nm, and/or the like.

Figure 9:
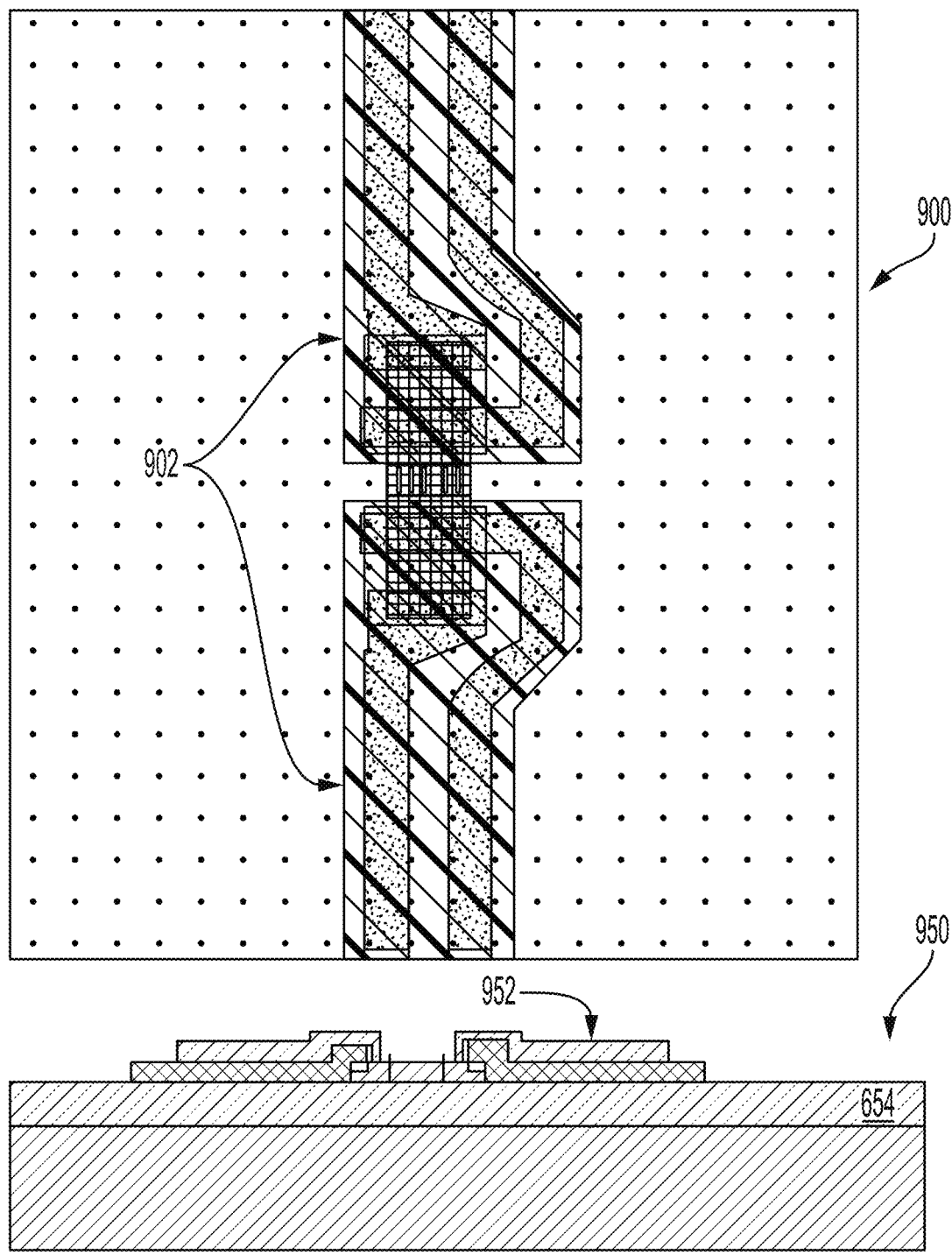
FIG. 9 is an exemplary diagram of an insulating layer (e.g., a thick insulating layer) overlaid on the nanowires, pads, and electrodes, and a corresponding side-view of the structure of FIG. 8 with the insulating layer, according to some embodiments.

FIG. 9 is an exemplary diagram 900 of an insulating layer 902 (e.g., a thick insulating layer) overlayed on the nanowires, pads, and electrodes, according to some embodiments. The schematic side-view of the structure 950 shows the insulating layer 952 deposited on the structure 850 from FIG. 8. In some embodiments, the insulator is a polymer. In some embodiments, the insulating layer 902 is about 10 nm, 50 nm, 100 nm, 150 nm, and/or the like thick. In some embodiments, the insulating layer is thicker than 100 nm. In certain embodiments, the insulating layer is thinner than 100 nm, but thicker than 30 nm. In some embodiments, the insulating layer is an oxide, such as $Al_2O_3$, $SiO_2$, or $HfO_2$. Photolithography can be used to define the area over which the insulator is placed. In some embodiments, the insulator is deposited with physical vapor deposition. In some embodiments, the insulator is deposited with atomic layer deposition. In some embodiments, multiple deposition techniques are used to create a stacked structure. The techniques described herein are not limited to the insulator materials, deposition methods, and/or stack geometries.

FIG. 10 shows an exemplary diagram 1000 of an insulating layer 1002 (e.g., a thin insulating layer) overlayed on the nanowires, according to some embodiments. The schematic side-view structure 1050 shows the thin insulating layer 1052 deposited on the structure 950 from FIG. 9. In some embodiments, the top insulating layer 1002 is approximately 10 nm, of a similar oxide as the first insulating layer. In some embodiments, the thickness of the insulating layer 1002 is less than 10 nm. In some embodiments, the insulating layer 1002 is between 10 and 30 nm. In some embodiments, the pads, electrodes, and/or first insulating layer are also coated with the insulating layer 1002 (e.g., on top of the previous insulating layer). In some embodiments, the insulator is an oxide, including but not limited to $Al_2O_3$, $SiO_2$, or $HfO_2$. In some embodiments, the insulator is a polymer. In some embodiments, the insulator is deposited with physical vapor deposition. In some embodiments, the insulator is deposited with atomic layer deposition. In some embodiments, multiple deposition techniques are used to create a stacked structure. The techniques described herein are not limited in terms of the insulator materials, deposition methods, and/or stack geometries.

Figure 11:
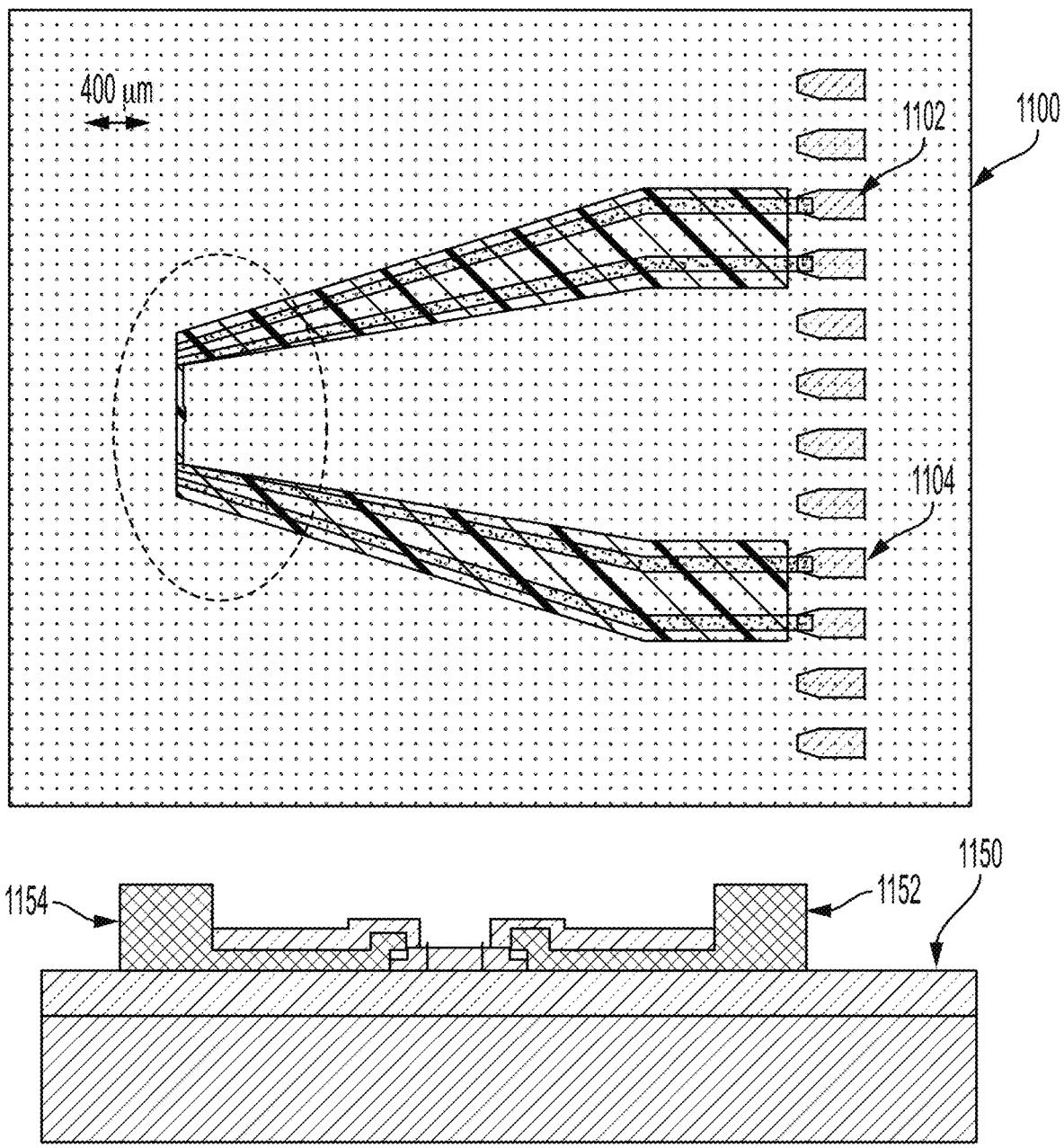
FIG. 11 is an exemplary diagram of the complete structure with final metal pads and a corresponding side-view of the structure of FIG. 10 with the final metal pads, according to some embodiments.

FIG. 11 is an exemplary diagram 1100 of the complete structure with final metal pads, including pads 1102 and 1104, according to some embodiments. As described herein, the pads are used to connect to external electronics for measurement and control purposes. The side-view structure 1150 shows the final metal pads 1152, 1154 deposited on the structure 1050 from FIG. 10. In some embodiments, the pads are between 0.5-4 microns thick, preferably 1 to 2 microns thick. In some embodiments, the pads are a highly conductive noble metal, such as Au, Ag, Cu. In some embodiments, an alloy is used. In certain embodiments, a multilayered metal structure is used. In some embodiments, the metal is deposited by physical vapor deposition. In certain embodiments, the electrodes are deposited using electron beam evaporation. It should be appreciated that the techniques are not limited in terms of possible metals or deposition techniques.

In some embodiments, the final metal deposition step involves deposition of extra electrodes for further sensor enhancements, for example, defining a reference electrode. In some embodiments, these enhancements are added in a later step.

As shown, the diagram 1100 includes extra pads, which in some embodiments connect to reference electrodes. Thus, diagram 1100 shows an example of a schematic of a finished sensor, ready for integration into a circuit. For example, the area 1106 represents where at least a portion of a fluid chamber can be located. The fluid to be analyzed is placed in the fluid chamber to expose the sensor to the fluid.

Figure 12:
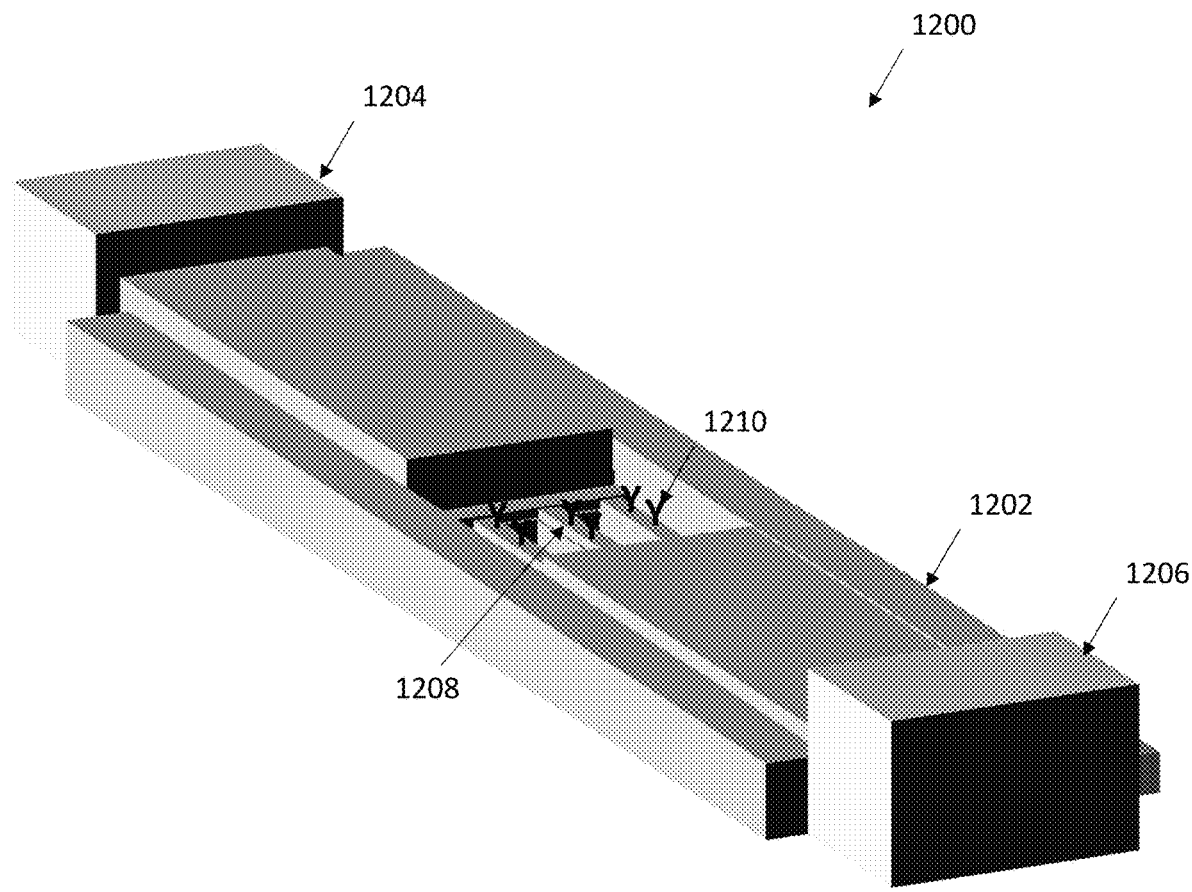
FIG. 12 is an exemplary diagram of an exemplary completed device with functionalized nanowires, according to some embodiments.

As described herein, the nanowires are functionalized with one or more detector species. In some embodiments, the detector is an antibody. In some embodiments, the detector is a DNA strand. FIG. 12 is a diagram of a representative completed device 1200 with functionalized nanowires. The electrodes are coated in thick insulating material 1202 except for the external electrode pads 1204, 1206. The nanowires 1208 are functionalized with receptor molecules 1210 for detecting an analyte.

While not shown, in some embodiments the fluid chamber is attached to the sensor device. The fluid chamber can be, for example, a half-ellipsoid sealed onto the sensor substrate. In some embodiments, the chamber is of a material such as paraffin wax. In some embodiments, a solid chamber, such as a glass chamber, is used. In some embodiments, the chamber is polyethylene. The techniques described herein are not limited in terms of chamber materials or shapes.

Figure 13:
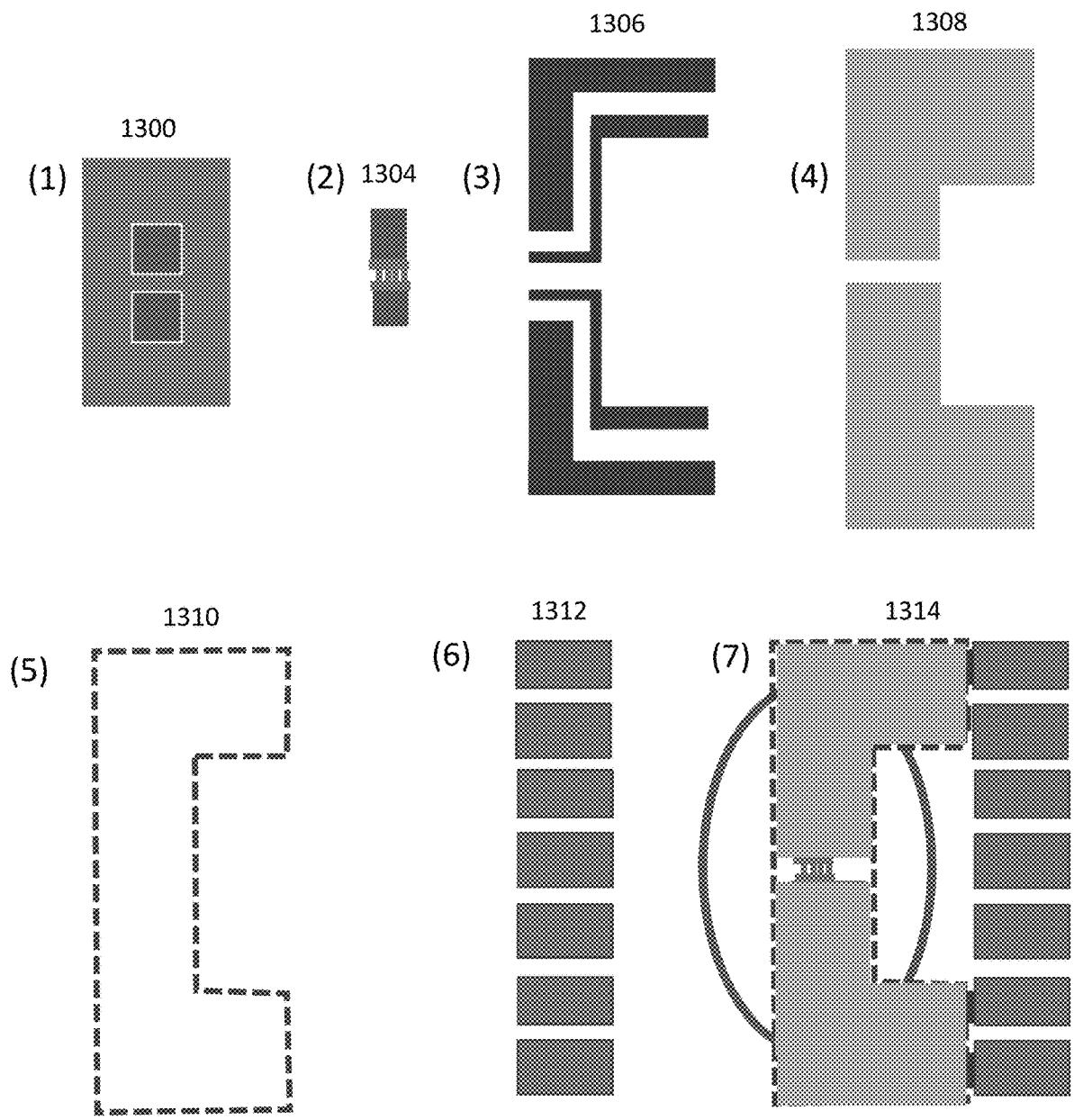
FIG. 13 is a drawing showing an example of the masks that can be used for the fabrication process steps described in conjunction with FIGS. 6-11, according to some embodiments.

FIG. 13 is a drawing of exemplary masks that can be used for the process steps described in conjunction with FIGS. 6-11, according to some embodiments. In particular, mask 1302 can be used for the process step discussed in conjunction with FIG. 6; mask 1304 can be used for the process step discussed in conjunction with FIG. 7; mask 1306 can be used for the process step discussed in conjunction with FIG. 8; mask 1308 can be used for the process step discussed in conjunction with FIG. 9; mask 1310 can be used for the process step discussed in conjunction with FIG. 10; and masks 1312 and 1314 can be used for the process step discussed in conjunction with FIG. 11.

Some embodiments relate to an enhanced microfluidic biomolecular sensor that allows measurement of the conductance of the fluid (e.g., simultaneously with the presence of analytes). Some embodiments relate to incorporating the fluid conductivity measurement onto the same chip as the biosensor, such as a FET biosensor as described herein.

Figure 14:
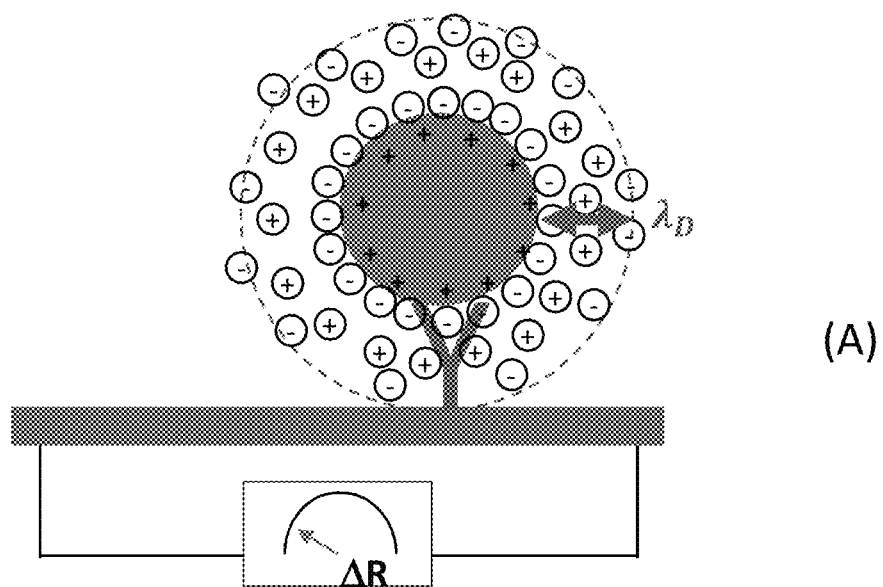
FIG. 14 is a diagram showing an analyte binding with a large background ionic concentration, and the same analyte binding under conditions of low background ionic concentration, according to some examples.
Figure 14:
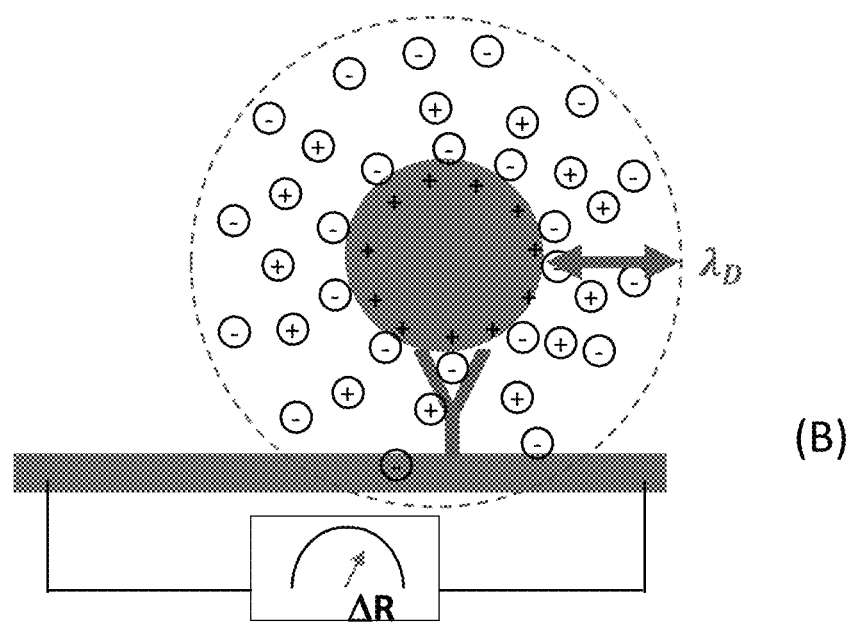

Most biological fluid samples, such as blood and sweat, are typically a complex mixture of water, proteins, and a variety of ions originating from dissociated salts and buffers. Some biomolecules have binding properties that depend on other ions that may be present in a fluid sample. For example, the fluid's ionic background may interfere with precision measurement and calibration of the sensor. Notably, the Debye length depends on the background ionic concentration. The Debye length is essentially the range of electrostatic influence of a given molecule when it is in solution. FIG. 14A illustrates an exemplary analyte binding with large background ionic concentration, showing no measurable electrical influence on the semiconductor. FIG. 14B illustrates the same exemplary analyte binding of FIG. 14A under conditions of low background ionic concentration, giving a measurable signal.

As shown by FIGS. 14A and 14B, proper calibration of the sensor can require precise knowledge of the background ionic concentration. The Debye length can be used to determine various parameters of the sensor. The Debye length can be used to determine how close an analyte should be to the semiconductor in a biosensor (e.g., a FET sensor) to produce a given signal. The Debye length can be used to determine what the signal will be for an analyte bound a given distance from the semiconductor surface. Low concentrations of analyte in a low-ionic-background solution may produce the same measured signal as high concentrations of analyte in a high-ionic-background solution. Therefore, for precision measurement and calibration utilizing FET biomolecular sensors, the background ionic concentration can be determined. The techniques described herein provide for direct measurement of the ionic concentration of a given sample to obtain information about the ionic concentration of the solution.

In some embodiments, being able to determine the background ionic concentration of a fluid sample can be used for interpreting sensor data, ruling out false positives and/or negatives, and/or for performing other measurements. In general, for dilute ions in a neutral fluid (e.g. electrolytes in water, or biological fluids such as blood and sweat), the ionic concentration is directly related to the fluid's electrical conductivity (or, equivalently, resistivity). In some embodiments, the ionic concentration of the fluid can be an additional marker for disease detection. For example, salt concentration in sweat can be a marker for cystic fibrosis.

Figure 15:
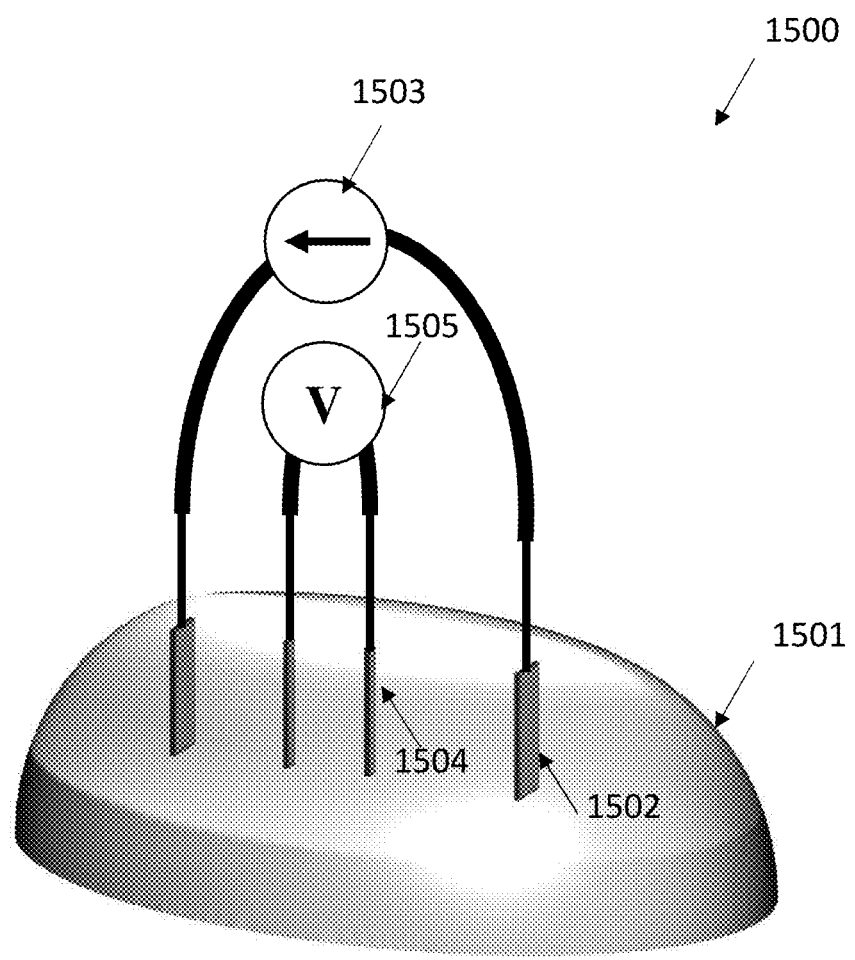
FIG. 15 is an schematic of an exemplary fluid conductance measurement configuration, according to some examples.

The techniques described herein provide an enhanced biosensor with integrated fluid conductance measurement capabilities. FIG. 15 shows a schematic diagram 1500 of an exemplary fluid conductance measurement configuration using an external conductance probe, according to some embodiments. FIG. 15 shows exemplary components for measuring the conductance of a fluid droplet 1501, including current electrodes 1502 attached to a current supply 1503. The current supply 1503 creates a constant electrical current I between the current electrodes 1502. Voltage electrodes 1504 are electrically connected to a measurement device 1505 (e.g., a volt meter), which measures the voltage V across the voltage electrodes. The fluid conductance G is proportional to I/V. The proportionality factor depends on the electrode geometry and can be determined using basic principles. For example, for a thin fluid layer with electrodes uniformly-spaced in a linear pattern, the proportionality is ln [2]/π.

Some embodiments relate to sensing the conductance of a fluid flow. If a fluid has charged molecules and is flowing over a sensor, then as the fluid flows, the local conductance at the sensor could change. As described herein, some sensor techniques relate to sensing the presence (or absence) of an analyte by sensing whether there is a change of voltage or conductance of the sensor when a solution is applied to the sensor. The inventors have discovered and appreciated that if the fluid is flowing over the sensor, if the solution includes charged molecules flowing through the fluid, the local conductance could change during the flow. This change of conductance may therefore not necessarily be the antigen/antibody binding events. Such a change in local conductance could incorrectly be interpreted to mean that an analyte is present in the solution when it is not present, or likewise may be incorrectly interpreted to mean that an analyte is not present in the solution when it is present. The inventors have therefore developed flow conductance sensing techniques, which can be used to monitor for and/or determine changes in fluid conductance while the fluid flows over the sensor area. In some embodiments, such techniques can be used to avoid having changes in the fluid conductance impact the detection of an analyte by a nanosensor. In some embodiments, such techniques can be used to sense the presence of an analyte (e.g., where the flow conductance device is the sensor, thus being used separate from a nanosensor).

The techniques described herein provide for using a set of measurement electrodes that are spaced along the fluid channel. By spacing the electrodes along/inside the fluid channel, as the charged particles move through the channel, the electrodes can be used to measure changes in the local conductance of the fluid. The fluid conductance can be related to the type, size and/or amount of biomolecules in the fluid. Different biomolecules may have different electrical characteristics. By measuring conductance differences/changes of the fluid, the techniques can be used to identify different biomolecule species. In some embodiments, flow conductance measurements can be used to determine particle counts. Field adjustment electrodes can be used (e.g., with the measurement electrodes) to provide better electrophoresis than may be otherwise exhibited by just the fluid.

Figure 17:
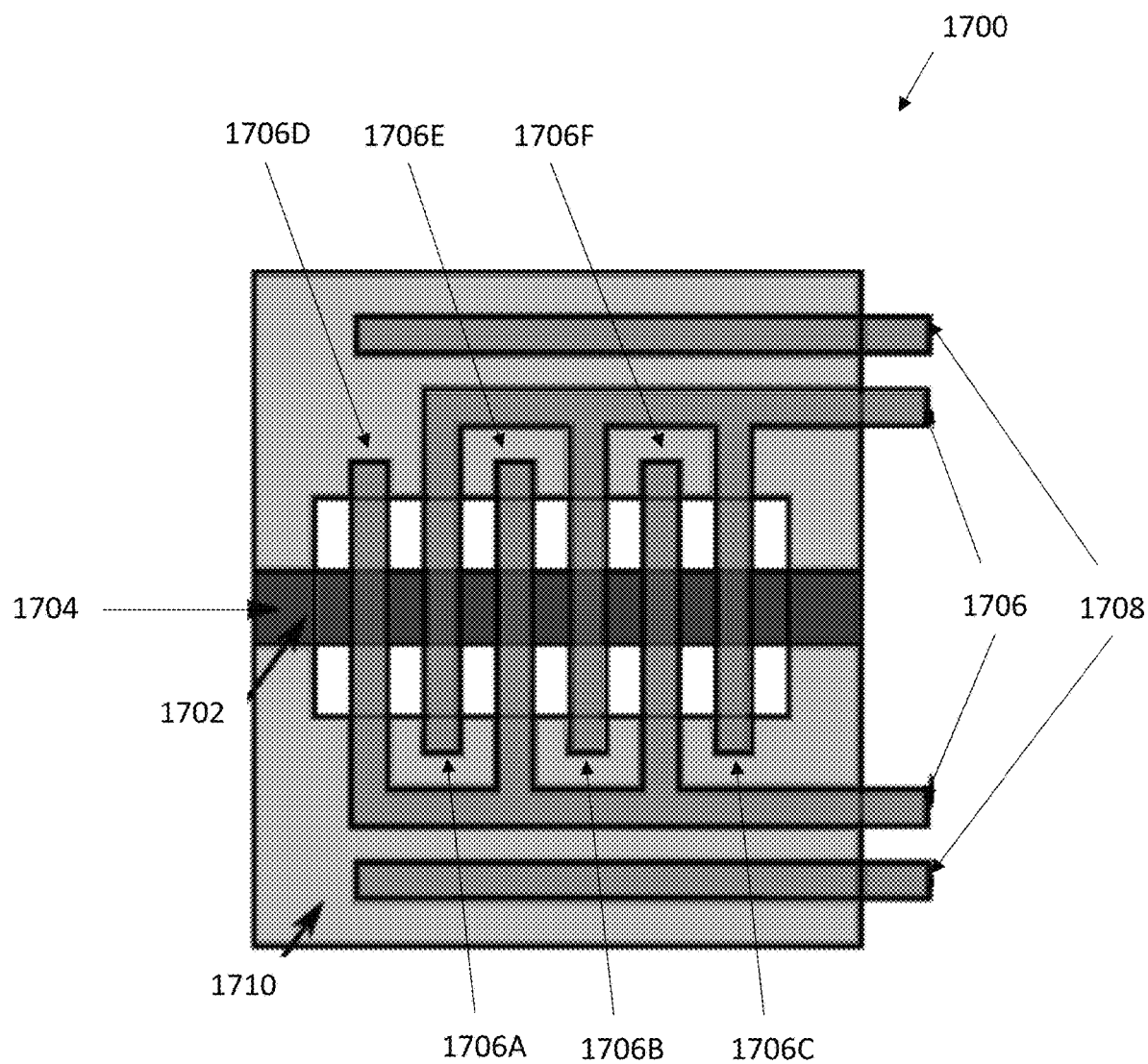
FIG. 17 is a diagram of an exemplary electrode configuration for measuring the changes in conductance of a fluid flow, according to some embodiments.

FIG. 17 is a diagram of an exemplary electrode configuration 1700 for measuring the changes in conductance of a fluid flow, according to some embodiments. The configuration 1700 includes a fluid channel 1702 through which a fluid (e.g., a solution including charged particles/hydrogel) flows in the direction indicated by 1704. The electrodes include measurement electrodes 1706 and field adjustment electrodes 1708. The measurement electrodes 1706 include a first set of electrodes 1706A, 1706B, and 1706C, and a second set of electrodes 1706D, 1706E and 1706F. The electrodes 1706 and 1708 are formed in an electrical insulation layer 1710 (e.g., silicon, as described herein). The fluid channel 1702 overlays the measurement electrodes 1706.

The electrical conductance change can be measured using the measurement electrodes 1706 as the solution flows over the measurement electrodes to determine fluid flow conductance measurement(s). As shown in this example, the first and second sets of electrodes are interdigit, such that each of the first set of electrodes are equally spaced among each other and each of the second set of electrodes are equally spaced among each other, and form interlocked fan-shaped arrays of electrodes. In the example shown in FIG. 17, each array of fan-shaped electrodes has a backbone that extends along the direction of the fluid channel and is spaced from the fluid channel on an associated side of the fluid channel. Each electrode of a particular array has a first end in electrical communication with the backbone and extends along a direction substantially orthogonal to the direction of the fluid channel such that the other end of each of the measurement electrode is disposed on the second side of the fluid channel. While the measurement electrodes 1706 in this example are shown to be equally spaced, the first set of measurement electrodes, the second set of measurement electrodes, or both can include different spacing configurations. While two sets of electrodes are shown, one set of electrodes can be used, three sets of electrodes, or any number of sets of electrodes can be used without departing from the techniques described herein.

The field adjustment electrodes 1708 can be used for electrophoresis. For example, a current can be applied to the field adjustment electrodes 1708 to create an electric field across the fluid chamber 1702, which can cause better movement of charged particles in the fluid along the direction shown by 1704. In some embodiments, applying an electric field using the field adjustment electrodes 1708, particles with different charges will flow through the fluid chamber 1702 at different speeds. Some embodiments can use information about the speed of the charged particles to separate apart different charged particles. As shown in FIG. 17, each field adjustment electrode extends along the direction of the fluid channel, and is disposed on an associated side of the fluid channel and is spaced further from the fluid channel than the backbone of the fan-shaped array of electrodes.

The measurement electrode 1706 can have various physical configurations, including various widths. For example, the sensors can be nanowires. In some embodiments, the sensors have widths of 100s of nanometers, millimeters, and/or the like. The measurement dimensions can be chosen based on the analyte and/or other property of the fluid being measured. Examples of the dimensions of the measurement electrodes 1706 can be on the order of 5-15 nm, a few microns, and/or the like. Prior to introduction of the fluid into the fluid chamber 1702, the measurement electrodes 1706 are spatially isolated from each other. For example, as shown in FIG. 17, the fan-shaped sets of electrodes are spatially isolated from each other. The measurement electrodes 1706 can be connected to a current source. Applying a current across the measurement electrodes 1706 with no fluid (or a fluid with no charged particles) will result in no current and/or a minimal current rating. When an electrolyte solution containing charged particles that has its own conductance is passed into the fluid chamber 1702, then that medium electrically connects the electrodes such that if a voltage or current is passed across the electrodes, the system can determine a resistance. The detected resistance can be proportional to the charged molecules in the solution.

The flow conductance measurement can be determined as a function of the concentration of charged particles and the speed at which they travel through the fluid chamber while under the influence of an electrical field. In some embodiments, different analytes can be separated (e.g., identified, separated from other analytes or particles, and/or the like) by their speed traveling through the fluid chamber under the influence of electric field. For example, particles carrying disparate charges and/or mass will typically travel at different speeds. In some embodiments, the speed of particles can be determined based on a comparison of conductance pulses at the time of flight/movement of the particles. When more than one category of charge-carrying particles is present in a solution, electrical fields of various strengths can be applied, and the resulting spectrums associated with each electrical field (which essentially creates a conductance spectrum) can be analyzed to separate the different particles.

In some embodiments, the measurement electrodes 1706 are disposed within the fluid channel 1702. In some embodiments, the measurement electrodes 1706 are insulated from the fluid flowing in the fluid channel 1702. For example, the device can include an insulation layer to isolate the measurement electrodes 1706 from the fluid channel 1702 (e.g., and therefore to isolate the measurement electrodes 1706 from other possible events).

The fluid or electrolyte containing the charged particles/hydrogel can be any solution that has charged particles. In some embodiments, the fluid can be blood and/or derived from blood (e.g., blood passed through a red blood cell filter to filter out the red blood cells) to measure biomolecules inside the blood sample. In some embodiments, a flow conductance sensor can be used on its own to detect an analyte (e.g., to detect large particles that cannot be measured by a nanosensor). In some embodiments, a flow conductance sensor can be used in conjunction with a nanosensor to provide for measuring particles of different sizes.

In some embodiments, the conductivity measurement techniques are used alone to sense an analyte. In some embodiments, the conductivity measurement is integrated onto the chip with the biosensor. Integrating the conductivity measurement components onto the chip can enable conductance measurements with no external probes. External probes may be too large for microscopic samples, may be mechanically unstable on a small device, and/or may not be implantable in the body should FET biomolecular sensors be used in such a manner.

In some embodiments, additional metal lines are added onto the biosensor substrate chip to create the current and voltage electrodes to add conductivity measurement to the biosensor chip. One end of the electrodes can be disposed inside the fluid region, and the other end can be disposed outside the fluid region. The end of the electrodes outside the fluid region can be connected to external measuring equipment, as described below. In some embodiments, the electrodes can exit the fluid region as a thin film on top of the sensor substrate. In some embodiments, the electrodes can use through silicon vias (TSV) and emerge at the bottom of the sensor substrate. It should be appreciated that the techniques described herein cover any possible electrode paths from the fluid to the measurement devices.

In some embodiments, the conductance of the fluid can be measured by applying a voltage or current and measuring the corresponding current or voltage. In some embodiments, a two-point measurement technique can be used to measure the fluid conductivity, where the current and voltage electrodes are the same as described herein. For example, for a two-point measurement configuration, the applied voltage can use the same electrodes as the measured current. In some embodiments, a four-point measurement is used to measure the fluid conductivity, which can use four electrodes (e.g., two extra electrodes that can be added for conductivity measurement that are separate from the voltage electrodes). For example, for a four-point configuration, a current is supplied between outer electrodes and the voltage across inner electrodes can be measured.

Various types of measurements can be used to determine the conductivity. In some embodiments, a direct-current (DC) measurement can be performed, where the current and voltage are constant in time. In some embodiments, an alternating current (AC) measurement can be performed, where both the current and voltage are sinusoidal in time. In some embodiments, AC measurement can be performed without the metal lines in direct contact with the fluid, which can allow for an insulating barrier to cover some or all of the electrodes.

The electrodes can include various configurations. In some embodiments, some or all of the electrodes are parallel. In some embodiments, the electrodes are interdigitated (e.g., as discussed in conjunction with FIG. 17). The techniques described herein are not limited in terms of electrode geometries and measurement techniques, including where electrodes are added directly to the sensor substrate.

The electrodes can be fabricated using various materials. In some embodiments, the electrodes are made from Pt. In some embodiments, the electrodes are Au. In some embodiments, the electrodes are metal or a metal alloy. The techniques described herein are not limited in terms of possible metals to be used in such electrodes.

The electrodes can have various dimensions, including various widths. In some embodiments, the electrodes are under 10 microns wide. In some embodiments, the electrodes are 10-100 microns wide. The electrodes can have different widths in a device. For example, for a four-point measurement embodiment, the voltage and current electrodes may be different widths. The techniques described herein are not limited in terms of possible electrode widths and width combinations.

In some embodiments, the electrodes are coated with an insulating material (e.g., when using an AC measurement technique). In some embodiments, the insulating material is $Al_2O_3$. In some embodiments, the insulating material is $HfO_2$. In some embodiments, the insulator is a multilayered structure of different insulating materials. The techniques described herein are not limited in terms of insulator materials and heterostructures.

Various fabrication techniques can be used to create a fluid conductance device in accordance with the techniques described herein. In some embodiments, the conductance-measurement electrodes are deposited during the same process step as the sensor electrodes. In some embodiments, the electrodes are deposited during a different process step. The techniques are not limited in terms of deposition processes and/or process integration steps.

Figure 16:
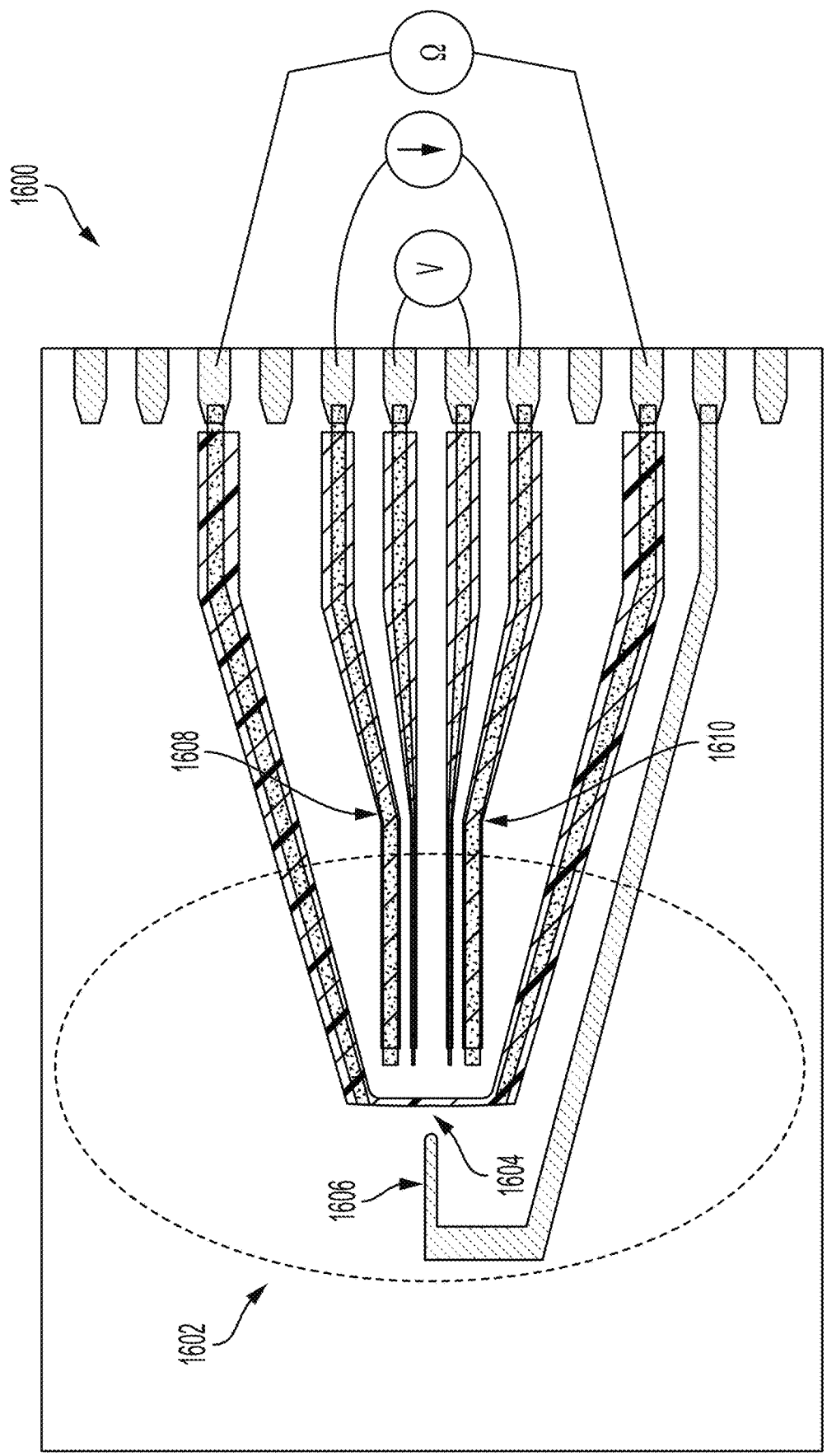
FIG. 16 is a schematic of an exemplary integrated FET biomolecular sensor design with fluid conductance measurement, according to some embodiments.

FIG. 16 is a diagram 1600 of an exemplary embodiment of a biosensor with an integrated on-chip conductivity measurement, according to some embodiments. The biosensor includes a fluid chamber (generally/approximately illustrated as 1602), a sensor 1604, a reference electrode 1606, and fluid conductance measurement electrodes 1608 and 1610 (among other electrodes).

The techniques described herein for fluid conductance measurement can be used to provide knowledge of the background fluid ionic concentration. The fluid ionic concentration can be used to make precision measurements of analyte binding in biomolecular sensors. Therefore, the techniques described herein can provide better sensing capabilities and data interpretation by incorporating the fluid conductance measurement.

Various computer systems can be used to perform any of the aspects of the techniques and embodiments disclosed herein. The computer system may include one or more processors and one or more non-transitory computer-readable storage media (e.g., memory and/or one or more non-volatile storage media) and a display. The processor may control writing data to and reading data from the memory and the non-volatile storage device in any suitable manner, as the aspects of the invention described herein are not limited in this respect. To perform functionality and/or techniques described herein, the processor may execute one or more instructions stored in one or more computer-readable storage media (e.g., the memory, storage media, etc.), which may serve as non-transitory computer-readable storage media storing instructions for execution by the processor.

In connection with techniques described herein, code used to, for example, provide the techniques described herein may be stored on one or more computer-readable storage media of computer system. Processor may execute any such code to provide any techniques for planning an exercise as described herein. Any other software, programs or instructions described herein may also be stored and executed by computer system. It will be appreciated that computer code may be applied to any aspects of methods and techniques described herein. For example, computer code may be applied to interact with an operating system to plan exercises for diabetic users through conventional operating system processes.

The various methods or processes outlined herein may be coded as software that is executable on one or more processors that employ any one of a variety of operating systems or platforms. Additionally, such software may be written using any of numerous suitable programming languages and/or programming or scripting tools, and also may be compiled as executable machine language code or intermediate code that is executed on a virtual machine or a suitable framework.

In this respect, various inventive concepts may be embodied as at least one non-transitory computer readable storage medium (e.g., a computer memory, one or more floppy discs, compact discs, optical discs, magnetic tapes, flash memories, circuit configurations in Field Programmable Gate Arrays or other semiconductor devices, etc.) encoded with one or more programs that, when executed on one or more computers or other processors, implement the various embodiments of the present invention. The non-transitory computer-readable medium or media may be transportable, such that the program or programs stored thereon may be loaded onto any computer resource to implement various aspects of the present invention as discussed above.

The terms "program," "software," and/or "application" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion among different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in non-transitory computer-readable storage media in any suitable form. Data structures may have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various inventive concepts may be embodied as one or more methods, of which examples have been provided. The acts performed as part of a method may be ordered in any suitable way. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This allows elements to optionally be present other than the elements specifically identified within the list of elements to which the phrase "at least one" refers, whether related or unrelated to those elements specifically identified.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting.

Various aspects are described in this disclosure, which include, but are not limited to, the above-described aspects.

The invention claimed is:

1. A device, comprising:
    at least one sensor element configured to sense an analyte, the at least one sensor element comprising a first contact pad and a second contact pad, wherein the at least one sensor element comprises at least one semiconductor sensor in electrical communication with a source and a drain, wherein the source and the drain comprise a semiconductor material;
    a first current electrode attached to the first contact pad and a second current electrode attached to the second contact pad; and
    a first measurement electrode attached to the first contact pad and a second measurement electrode attached to the contact pad,
    wherein the first contact pad is in electrical communication with the source and comprises a first portion and a second portion different than the first portion, wherein the first portion overlaps the source;
    wherein the second contact pad is in electrical communication with the drain and comprises a first portion and a second portion different than the first portion, wherein the first portion overlaps the drain; and
    wherein the first portions are ion-implanted and the second portions are not ion-implanted.

2. The device of claim 1, wherein the first portions of the first and second contact pads comprise ion-implanted electrode attachment pads.

3. The device of claim 2, wherein the ions comprise one or more Group III and/or Group V elements.

4. The device of claim 2, wherein the ions comprise a metal.

5. The device of claim 1, wherein:
    the first current electrode is attached to the first portion of the first contact pad and the first measurement electrode is attached to the second portion of the first contact pad that is different than the first portion of the first contact pad;
    the second current electrode is attached to the first portion of the second contact pad and the second measurement electrode is attached to the second portion of the second contact pad that is different than the first portion of the second contact pad.

6. The device of claim 1, wherein:
    the source and drain each comprise a first portion proximate to the at least one semiconductor sensor and a second portion distal to the at least one semiconductor sensor;
    the first current electrode is attached to the second portion of the source and the second current electrode is attached to the second portion of the drain; and
    the first measurement electrode is attached to the first portion of the source and the second measurement electrode is attached to the first portion of the drain.

7. The device of claim 1, further comprising a measurement device in electrical communication with the first measurement electrode and the second measurement electrode.

8. The device of claim 7, wherein the measurement device comprises a voltmeter.

9. The device of claim 1, further comprising a current source in electrical communication with the first current electrode and the second current electrode.

* * * * *